United States Patent
Stace et al.

(10) Patent No.: US 9,932,367 B2
(45) Date of Patent: Apr. 3, 2018

(54) MODIFICATION OF POLYPEPTIDES

(71) Applicant: BicycleRD Limited, Cambridge (GB)

(72) Inventors: Catherine Stace, Cambridge (GB);
Edward Walker, Cambridge (GB)

(73) Assignee: BICYCLERD LIMITED, Cambridge (GB)

( * ) Notice: Subject to any disclaimer, the term of this patent is extended or adjusted under 35 U.S.C. 154(b) by 133 days.

(21) Appl. No.: 14/849,637

(22) Filed: Sep. 10, 2015

(65) Prior Publication Data

US 2016/0031939 A1 Feb. 4, 2016

Related U.S. Application Data

(63) Continuation-in-part of application No. PCT/EP2014/055204, filed on Mar. 14, 2014, which is a continuation of application No. 13/832,526, filed on Mar. 15, 2013, now abandoned.

(51) Int. Cl.
| | |
|---|---|
| C40B 50/14 | (2006.01) |
| C07K 7/06 | (2006.01) |
| G01N 33/68 | (2006.01) |
| C12N 15/10 | (2006.01) |
| C07K 1/107 | (2006.01) |

(52) U.S. Cl.
CPC .............. *C07K 7/06* (2013.01); *C07K 1/1072* (2013.01); *C12N 15/1037* (2013.01); *G01N 33/6803* (2013.01); *C40B 50/14* (2013.01)

(58) Field of Classification Search
None
See application file for complete search history.

(56) References Cited

U.S. PATENT DOCUMENTS

| | | | |
|---|---|---|---|
| 8,685,890 B2 | 4/2014 | Winter et al. | |
| 8,778,844 B2 | 7/2014 | Winter et al. | |
| 2012/0101253 A1 | 4/2012 | Heinis et al. | |
| 2012/0101256 A1 | 4/2012 | Winter et al. | |
| 2012/0142541 A1 | 6/2012 | Winter et al. | |
| 2014/0163201 A1 | 6/2014 | Winter et al. | |

FOREIGN PATENT DOCUMENTS

WO 2010/089115 12/2010

OTHER PUBLICATIONS

International Preliminary Report on Patentability and Written Opinion of the International Searching Authority dated Sep. 15, 2015, which issued during prosecution of International Application No. PCT/EP2014/055204.

International Search Report and Written Opinion of the International Searching Authority dated Jun. 4, 2014, which issued during prosecution of International Application No. PCT/EP2014/055204.

Angelini, et al. "Bicyclic Peptide Inhibitor Reveals Large Contact Interface with a Protease Target" ACS Chemical Biology, May 2012, 7(5):817-821.

(Continued)

*Primary Examiner* — Christian C Boesen
(74) *Attorney, Agent, or Firm* — Vedder Price P.C.; Thomas J. Kowalski; Deborah L. Lu

(57) ABSTRACT

The invention provides a method for conjugating a peptide displayed on a genetic display system to a molecular scaffold performed on an ion exchange resin.

13 Claims, 10 Drawing Sheets

(56) References Cited

OTHER PUBLICATIONS

Baeriswyl, et al. "Bicyclic Peptides with Optimized Ring Size Inhibit Human Plasma Kallikrein and its Orthologues While Sparing Paralogous Proteases" Chemmedchem, Apr. 2012, 7(7):1173-1176.

Finucane, et al. "Core-Directed Protein Design. I. An Experimental Method for Selecting Stable Proteins from Combinatorial Libraries" Biochemistry, Sep. 1999, 38(36):11604-11612.

Goodridge, et al. "Simultaneous Water Quality Monitoring and Fecal Pollution Source Tracking in the Colorado Big Thompson Water Project" Completion Report No. 219, Colorado Water Institute, Dec. 2009.

Heinis, et al. "Phage-encoded combinatorial chemical libraries based on bicyclic peptides" Nature Chemical Biology, May 2009, 5(7):502-507.

Ng, et al. "Quantitative Synthesis of Genetically Encoded Glycopeptide Libraries displayed on M13 Phage" ACS Chemical Biology, Jun. 2012, 7(9):1482-1487.

Touati et al. "Phage Selection of Bicyclic Peptide Ligands and Development of a New Peptide Cyclisation Method" These No. 5536, Oct. 2012, retrieved from: http://infoscience.epfl.ch/record/181662/files/EPFL_TH5536.pdf.

Urbanelli, et al. "Targeted Gene Transduction of Mammalian Cells Expressing the HER2/neu Receptor by Filamentous Phage" Journal of Molecular Biology, Nov. 2001, 313(5):965-976.

Siegel, et al. "Isolation of cell-surface-specific human monoclonal antibodies using phage display and magnetically-activated cell sorting: applications in immunohematology" Journal of Immunological Methods 206:73-85, 1997.

Notification of Second Office Action dated Nov. 24, 2017, which issued during prosecution of Chinese Application No. 2017112102187430.

Notification of Reasons for Refusal dated Dec. 1, 2017, which issued during prosecution of Japanese Application No. 2015-562247.

Hofmann, et al. "In Vitro Selection of Functional Lantipeptide" Journal of American Chemical Society, 2012, 134:8038-8041.

Monjezi, et al. "Purification of bacteriophage M13 by anion exchange chromatography" Journal of Chromatography B, 2010, 878(21):1855-1859.

Schlippe, et al. "In Vitro Selection of Highly Modified Cyclic peptide that Act as Tight Binding Inhibitors" Journal of American Chemical Society, 2012, 134(25):10469-10477.

FIGURE1A
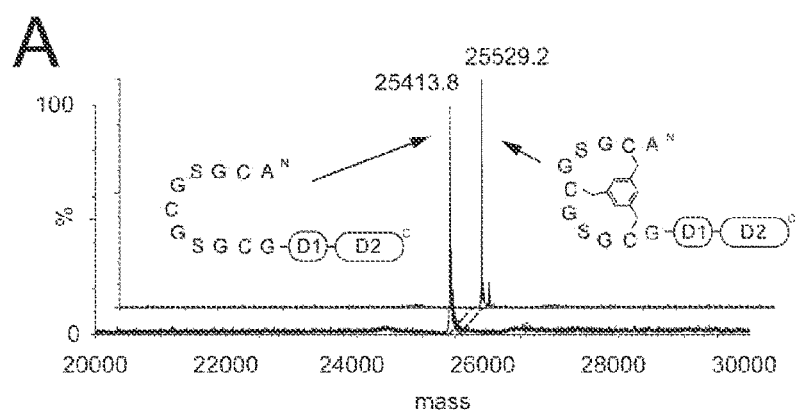
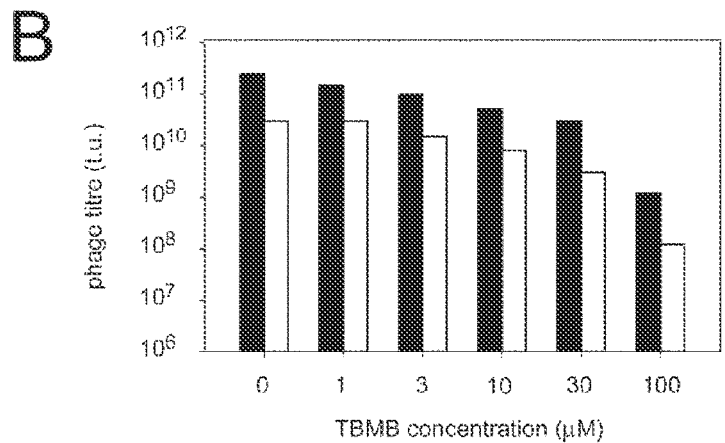
FIGURE 1B

A: 'Quick':

Wash beads in 1M
NaHCO3, add TCEP,
then add culture

B: 'Long':

SEQUENCE LISTING

```
<160> NUMBER OF SEQ ID NOS: 19

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      Combinatorial Library peptide
<220> FEATURE:
<221> NAME/KEY: MOD_RES
<222> LOCATION: (2)..(7)
<223> OTHER INFORMATION: Any amino acid
<220> FEATURE:
<221> NAME/KEY: MOD_RES
<222> LOCATION: (9)..(14)
<223> OTHER INFORMATION: Any amino acid

<400> SEQUENCE: 1

Cys Xaa Xaa Xaa Xaa Xaa Xaa Cys Xaa Xaa Xaa Xaa Xaa Xaa Cys
```

-continued

```
<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (1)..(1)
<223> OTHER INFORMATION: Any reactive amino acid; See specification as
      filed for detailed description of substitutions and preferred
      embodiments
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (5)..(5)
<223> OTHER INFORMATION: Any reactive amino acid; See specification as
      filed for detailed description of substitutions and preferred
      embodiments
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any reactive amino acid; See specification as
      filed for detailed description of substitutions and preferred
      embodiments

<400> SEQUENCE: 2

Xaa Phe Xaa Xaa Xaa Arg Val Xaa Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide ligand first loop consensus sequence
<220> FEATURE:
<221> NAME/KEY: MOD_RES
<222> LOCATION: (1)..(1)
<223> OTHER INFORMATION: Any reactive amino acid; See specification as
      filed for detailed description of substitutions and preferred
      embodiments
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (7)..(7)
<223> OTHER INFORMATION: Any reactive amino acid; See specification as
      filed for detailed description of substitutions and preferred
      embodiments

<400> SEQUENCE: 3

Xaa Gly Gly Xaa Xaa Asn Xaa
1               5

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
```

```
            consensus peptide
<220> FEATURE:
<221> NAME/KEY: MOD_RES
<222> LOCATION: (1)..(1)
<223> OTHER INFORMATION: Any reactive amino acid; See specification as
      filed for detailed description of substitutions and preferred
      embodiments
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (7)..(7)
<223> OTHER INFORMATION: Any reactive amino acid; See specification as
      filed for detailed description of substitutions and preferred
      embodiments
<220> FEATURE:
<221> NAME/KEY: MOD_RES
<222> LOCATION: (9)..(12)
<223> OTHER INFORMATION: Any amino acid
<220> FEATURE:
<221> NAME/KEY: MOD_RES
<222> LOCATION: (13)..(13)
<223> OTHER INFORMATION: Any reactive amino acid; See specification as
      filed for detailed description of substitutions and preferred
      embodiments

<400> SEQUENCE: 4

Xaa Gly Gly Xaa Xaa Asn Xaa Arg Xaa Xaa Xaa Xaa Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      motif of first loop of synthetic peptide ligand
<220> FEATURE:
<221> NAME/KEY: MOD_RES
<222> LOCATION: (1)..(1)
<223> OTHER INFORMATION: Any reactive amino acid; See specification as
      filed for detailed description of substitutions and preferred
      embodiments
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Trp or Phe
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Lys or Arg
<220> FEATURE:
<221> NAME/KEY: MOD_RES
<222> LOCATION: (7)..(7)
<223> OTHER INFORMATION: Any reactive amino acid; See specification as
      filed for detailed description of substitutions and preferred
      embodiments

<400> SEQUENCE: 5

Xaa Xaa Xaa Pro Xaa Xaa Xaa
1               5

<210> SEQ ID NO 6
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      construct - Peptide ligand loop motif
<220> FEATURE:
<221> NAME/KEY: MOD_RES
<222> LOCATION: (1)..(1)
<223> OTHER INFORMATION: Any reactive amino acid; See specification as
      filed for detailed description of substitutions and preferred
      embodiments
<220> FEATURE:
<221> NAME/KEY: MOD_RES
<222> LOCATION: (2)..(2)
<223> OTHER INFORMATION: Thr or Leu
<220> FEATURE:
<221> NAME/KEY: MOD_RES
<222> LOCATION: (4)..(4)
<223> OTHER INFORMATION: Gln or Thr
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Any reactive amino acid; See specification as
      filed for detailed description of substitutions and preferred
      embodiments

<400> SEQUENCE: 6

Xaa Xaa His Xaa Xaa Leu Xaa
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      construct - Example of first loop of peptide ligand
<220> FEATURE:
<221> NAME/KEY: MOD_RES
<222> LOCATION: (1)..(1)
<223> OTHER INFORMATION: Any reactive amino acid; See specification as
      filed for detailed description of substitutions and preferred
      embodiments
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (7)..(7)
<223> OTHER INFORMATION: Any reactive amino acid; See specification as
      filed for detailed description of substitutions and preferred
      embodiments

<400> SEQUENCE: 7

Xaa Xaa Trp Pro Ala Arg Xaa
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      construct - Example of first loop of peptide ligand
<220> FEATURE:
<221> NAME/KEY: MOD_RES
<222> LOCATION: (1)..(1)
<223> OTHER INFORMATION: Any reactive amino acid; See specification as
      filed for detailed description of substitutions and preferred
      embodiments
<220> FEATURE:
```

```
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (7)..(7)
<223> OTHER INFORMATION: Any reactive amino acid; See specification as
      filed for detailed description of substitutions and preferred
      embodiments

<400> SEQUENCE: 8

Xaa Xaa Trp Pro Ser Arg Xaa
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      construct - Example of first loop of peptide ligand
<220> FEATURE:
<221> NAME/KEY: MOD_RES
<222> LOCATION: (1)..(1)
<223> OTHER INFORMATION: Any reactive amino acid; See specification as
      filed for detailed description of substitutions and preferred
      embodiments
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (7)..(7)
<223> OTHER INFORMATION: Any reactive amino acid; See specification as
      filed for detailed description of substitutions and preferred
      embodiments

<400> SEQUENCE: 9

Xaa Xaa Phe Pro Phe Arg Xaa
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      construct - Example of first loop of peptide ligand
<220> FEATURE:
<221> NAME/KEY: MOD_RES
<222> LOCATION: (1)..(1)
<223> OTHER INFORMATION: Any reactive amino acid; See specification as
      filed for detailed description of substitutions and preferred
      embodiments
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (7)..(7)
<223> OTHER INFORMATION: Any reactive amino acid; See specification as
      filed for detailed description of substitutions and preferred
      embodiments

<400> SEQUENCE: 10

Xaa Xaa Phe Pro Tyr Arg Xaa
1               5

<210> SEQ ID NO 11
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      motif of first loop of synthetic peptide ligand
<220> FEATURE:
<221> NAME/KEY: MOD_RES
<222> LOCATION: (1)..(1)
<223> OTHER INFORMATION: Any reactive amino acid; See specification as
      filed for detailed description of substitutions and preferred
      embodiments
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(7)
<223> OTHER INFORMATION: Any reactive amino acid; See specification as
      filed for detailed description of substitutions and preferred
      embodiments

<400> SEQUENCE: 11

Xaa Xaa His Xaa Asp Leu Xaa
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      motif of first loop of synthetic peptide ligand
<220> FEATURE:
<221> NAME/KEY: MOD_RES
<222> LOCATION: (1)..(1)
<223> OTHER INFORMATION: Any reactive amino acid; See specification as
      filed for detailed description of substitutions and preferred
      embodiments
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (7)..(7)
<223> OTHER INFORMATION: Any reactive amino acid; See specification as
      filed for detailed description of substitutions and preferred
      embodiments

<400> SEQUENCE: 12

Xaa Thr His Xaa Xaa Leu Xaa
1               5

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      motif peptide
<220> FEATURE:
<221> NAME/KEY: MOD_RES
<222> LOCATION: (1)..(1)
<223> OTHER INFORMATION: Any reactive amino acid; See specification as
      filed for detailed description of substitutions and preferred
      embodiments
<220> FEATURE:
<221> NAME/KEY: MOD_RES
<222> LOCATION: (2)..(2)
<223> OTHER INFORMATION: Any amino acid
<220> FEATURE:
```

```
<221> NAME/KEY: MOD_RES
<222> LOCATION: (3)..(3)
<223> OTHER INFORMATION: Trp or Phe
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Lys or Arg
<220> FEATURE:
<221> NAME/KEY: MOD_RES
<222> LOCATION: (7)..(7)
<223> OTHER INFORMATION: Any reactive amino acid; See specification as
      filed for detailed description of substitutions and preferred
      embodiments
<220> FEATURE:
<221> NAME/KEY: MOD_RES
<222> LOCATION: (8)..(8)
<223> OTHER INFORMATION: Thr or Leu
<220> FEATURE:
<221> NAME/KEY: MOD_RES
<222> LOCATION: (10)..(10)
<223> OTHER INFORMATION: Gln or Thr
<220> FEATURE:
<221> NAME/KEY: MOD_RES
<222> LOCATION: (13)..(13)
<223> OTHER INFORMATION: Any reactive amino acid; See specification as
      filed for detailed description of substitutions and preferred
      embodiments

<400> SEQUENCE: 13

Xaa Xaa Xaa Pro Xaa Xaa Xaa Xaa His Xaa Asp Leu Xaa
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      N-terminal fusion peptide

<400> SEQUENCE: 14

Gly Cys Gly Ser Gly Cys Gly Ser Gly Cys Gly
1               5                   10

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(8)
<223> OTHER INFORMATION: Any natural amino acid and this region may
      encompass 3-6 residues, wherein some positions may be absent
<220> FEATURE:
<221> NAME/KEY: MOD_RES
<222> LOCATION: (10)..(15)
<223> OTHER INFORMATION: Any natural amino acid and this region may
      encompass 3-6 residues, wherein some positions may be absent
<220> FEATURE:
<223> OTHER INFORMATION: See specification as filed for detailed
      description of substitutions and preferred embodiments

<400> SEQUENCE: 15

Ala Cys Xaa Xaa Xaa Xaa Xaa Xaa Cys Xaa Xaa Xaa Xaa Xaa Xaa Cys
1               5                   10                  15

Gly
```

```
<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      N-terminal fusion peptide

<400> SEQUENCE: 16

Ala Gly Ser Gly Cys Gly Ser Gly Cys Gly
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      N-terminal fusion peptide

<400> SEQUENCE: 17

Ala Gly Ser Gly Lys Gly Ser Gly Cys Gly
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide PK15

<400> SEQUENCE: 18

Ala Cys Ser Asp Arg Phe Arg Asn Cys Pro Ala Asp Glu Ala Leu Cys
1               5                   10                  15
Gly

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      N-terminal fusion peptide

<400> SEQUENCE: 19

Ala Cys Gly Ser Gly Cys Gly Ser Gly Cys Gly
1               5                   10
```

MODIFICATION OF POLYPEPTIDES

RELATED APPLICATIONS AND INCORPORATION BY REFERENCE

This application is a continuation-in-part application of international patent application Serial No. PCT/EP2014/055204 filed 14 Mar. 2014, which published as PCT Publication No. WO 2014/140342 on 18 Sep. 2014, which claims benefit of U.S. patent application Ser. No. 13/832,526 filed 15 Mar. 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Sep. 25, 2015, is named 45768_01_2002_SL.txt and is 12,329 bytes in size.

FIELD OF THE INVENTION

The present invention concerns methods for production of polypeptide ligands having a desired binding activity. In particular, the invention concerns the production of polypeptides which are covalently bound to molecular scaffolds such that two or more peptide loops are subtended between attachment points to the scaffold. Attachment of the molecular scaffold to the polypeptide is performed on a purification resin, which can take the form of magnetic resin beads.

BACKGROUND OF THE INVENTION

Cyclic peptides are able to bind with high affinity and target specificity to protein targets and hence are an attractive molecule class for the development of therapeutics. In fact, several cyclic peptides are successfully used in the clinic, as for example the antibacterial peptide vancomycin, the immunosuppressant drug cyclosporine or the anti-cancer drug ocreotide (Driggers, et al., *Nat Rev Drug Discov* 2008, 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 $Å^2$; Wu, B., et al., *Science* 330 (6007), 1066-71), a cyclic peptide with the Arg-Gly-Asp motif binding to integrin αVb3 (355 $Å^2$) (Xiong, J. P., et al., *Science* 2002, 296 (5565), 151-5) or the cyclic peptide inhibitor upain-1 binding to urokinase-type plasminogen activator (603 $Å^2$; Zhao, G., et al., *J Struct Biol* 2007, 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8, MMP-8) which lost its selectivity over other MMPs when its ring was opened (Cherney, R. J., et al., *J Med Chem* 1998, 41 (11), 1749-51). The favorable binding properties achieved through macrocyclization are even more pronounced in multicyclic peptides having more than one peptide ring as for example in vancomycin, nisin or actinomycin.

Different research teams have previously tethered polypeptides with cysteine residues to a synthetic molecular structure (Kemp, D. S. and McNamara, P. E., J. Org. Chem, 1985; Timmerman, P. et al., ChemBioChem, 2005). Meloen and co-workers had used tris(bromomethyl)benzene and related molecules for rapid and quantitative cyclisation of multiple peptide loops onto synthetic scaffolds for structural mimicry of protein surfaces (Timmerman, P. et al., ChemBioChem, 2005). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

WO2004/077062 discloses a method of selecting a candidate drug compound. In particular, this document discloses various scaffold molecules comprising first and second reactive groups, and contacting said scaffold with a further molecule to form at least two linkages between the scaffold and the further molecule in a coupling reaction.

WO2006/078161 discloses binding compounds, immunogenic compounds and peptidomimetics. This document discloses the artificial synthesis of various collections of peptides taken from existing proteins. These peptides are then combined with a constant synthetic peptide having some amino acid changes introduced in order to produce combinatorial libraries. By introducing this diversity via the chemical linkage to separate peptides featuring various amino acid changes, an increased opportunity to find the desired binding activity is provided. FIG. 1 of this document shows a schematic representation of the synthesis of various loop peptide constructs. The constructs disclosed in this document rely on —SH functionalised peptides, typically which may comprise cysteine residues, and heteroaromatic groups on the scaffold, typically which may comprise benzylic halogen substituents such as bis- or tris-bromophenyl-benzene. Such groups react to form a thioether linkage between the peptide and the scaffold.

Heinis et al. recently developed a phage display-based combinatorial approach to generate and screen large libraries of bicyclic peptides to targets of interest (Heinis, et al., *Nat Chem Biol* 2009, 5 (7), 502-7; see also international patent application WO2009/098450). Briefly, combinatorial libraries of linear peptides containing three cysteine residues and two regions of six random amino acids (Cys-(Xaa)$_6$-Cys-(Xaa)$_6$-Cys) (SEQ ID NO: 1) were displayed on phage and cyclised by covalently linking the cysteine side chains to a small molecule (tris-(bromomethyl)benzene). Bicyclic peptides isolated in selections for affinity to the human proteases cathepsin G and plasma Kallikrein (PK) had nanomolar inhibitory constants. The best inhibitor, PK15, inhibits human PK (hPK) with a $K_i$ of 3 nM. Similarities in the amino acid sequences of several isolated bicyclic peptides suggested that both peptide loops contribute to the binding. PK15 did not inhibit rat PK (81% sequence identity) nor the homologous human serine proteases factor XIa (hfXIa; 69% sequence identity) or thrombin (36% sequence identity) at the highest concentration tested (10 μM) (Heinis, et al., *Nat Chem Biol* 2009, 5 (7), 502-7). This finding suggested that the bicyclic inhibitor possesses high affinity for its target, and is highly specific.

Although the method disclosed by Heinis et al. is effective for the modification of displayed polypeptide ligands to produce bicyclic peptides, its efficiency is very low. For example, infective phage are generated at a rate of only 1 in 350 per starting phage particle. We have therefore developed an improved protocol for the modification of polypeptide ligands displayed on genetic display systems.

Citation or identification of any document in this application is not an admission that such document is available as prior art to the present invention.

SUMMARY OF THE INVENTION

In a first aspect, the present invention provides a method for conjugating a peptide displayed on a genetic display system to a molecular scaffold, which may comprise the steps of:
  (a) combining polypeptides displayed on a genetic display system with a purification resin such that the display system is bound to the resin and treating the bound display system with a reducing agent;
  (b) exposing the bound display system to the molecular scaffold;
  (c) removing unreacted molecular scaffold from the bound display system; and
  (d) eluting the display system from the purification resin.

The original method by Heinis et al. performed the conjugation of peptide and molecular scaffold (TBMB) in free solution. Phage, bearing peptides which were (or were not) conjugated to the TBMB scaffold were then isolated by centrifugation. We have obtained improved results by conjugating the phage to a solid phase purification resin, which can then be used to isolate the phage. For example, the resin can be isolated by centrifugation or retained in columns; in a preferred embodiment, the resin is magnetic and can be isolated by the application of a magnetic field.

Heinis et al. obtained better results for the conjugation of peptide and molecular scaffold (TBMB) using disulphide-free phage. Using the techniques set forth herein, we have obtained improved results, bettering the results obtained by Heinis et al., by conjugating the polypeptide to wild-type pIII coat protein such that it is displayed on a phage particle.

Although wild-type pIII is subject to degradation of disulphide bonds by the reducing agent used in the procedure to couple the molecular scaffold to the polypeptide, we have found that the increased infectivity of wild-type pIII-bearing phage over disulphide-free phage more than compensates for any loss in activity resulting from the degradation of disulphide bonds.

Preferably, the polypeptide is displayed by fusion to the pIII protein of fd phage, such as fd-tet phage.

In embodiments, the genetic display system is selected from phage display, ribosome display, mRNA display, yeast display and bacterial display. In one embodiment, the genetic display system is phage display.

In one embodiment, step (a) is followed by a washing step before addition of the molecular scaffold. Washing can be performed, for example, with a solution of a reducing agent, for example the reducing agent used in step (a). Advantageously, the reducing agent used in the washing step is less powerful or more dilute than the reducing agent used in step (a).

The reducing agent used in step (a) is preferably included at a concentration of less than 500 mM, preferably less than 200 mM, advantageously less than 100 mM. For example, the reducing agent is present at a concentration of 10 mM or less, such as 1 mM.

The reducing agent in step (b) is preferably included at a concentration of less than 500 μM, preferably less than 2001 μM, advantageously less than 100 μM. For example, the reducing agent is present at a concentration of 10 μM or less, such as 1 μM.

The resin-bound polypeptides may be exposed to the reducing agent in purified form, or can be present in culture. Genetic display systems involve replication in cells, such as bacteria or yeast; these cells may be removed by purification, in which case step (a) may comprise a washing step, in which polypeptides bound to resin are washed in buffer and separated from the cell culture contaminants.

A suitable reducing agent is TCEP. Other reducing agents, such as DTT, can be used as set forth herein.

The reduction and conjugation reactions are preferably conducted at room temperature, such as 25° C. In some embodiments, the conjugation reaction may be conducted at 30° C. In the aforementioned method of Heinis et al., reactions are conducted at temperatures above room temperature, for example 42° C.

The reduction and conjugation reactions are advantageously conducted for a period of time of less than one hour. For example, the reactions may be conducted for 30 minutes, 20 minutes, 15 minutes or 10 minutes.

The polypeptide is preferably a polypeptide which may comprise at least three reactive groups, separated by at least two sequences which can form the "loops" of the polypeptide once conjugated to the molecular scaffold. The loops may be any suitable length, such as two, three, four, five, six, seven or more amino acids long. The loops may be the same length, or different. Preferably, at least two loops are provided. In some embodiments, three, four, five, six or more loops may be present.

Reactive groups in the polypeptide are capable of forming covalent linkages with the scaffold. Most commonly, reactive groups may comprise cysteine residues.

Peptides are combined with a purification resin, which can be any suitable resin which is useful as a solid phase for the purification of protein material. Many resins, such as ion-exchange resins including beads and chromatography materials are known in the art which are useful for this purpose.

In an advantageous embodiment, the resin is a magnetic resin, which allows magnetic separation of the polypeptides bound to the genetic display system.

The scaffold may be any structure which provides multiple attachment points for the reactive groups of the polypeptide. Exemplary scaffolds are described below. Scaffold molecules are conjugated to the polypeptide whilst the polypeptides are incorporated into the genetic display system, such that the genetic display system displays the polypeptide ligand including the molecular scaffold. Excess scaffold is removed.

After the scaffold has been conjugated to the polypeptides, the genetic display systems incorporating the polypeptide ligands are eluted from the resin. The polypeptides can then be displayed on the genetic display system in conjugated form, and selected by known means.

In embodiments, the polypeptide ligands are multispecific. In a first configuration, for example, the polypeptide loops formed by the interaction of the polypeptide with the molecular scaffold are capable of binding to more than one target. Within this configuration, in one embodiment loops may be selected individually for binding to the desired targets, and then combined. In another embodiment, the loops are selected together, as part of a single structure, for binding to different desired targets.

In a second configuration, a functional group may be attached to the N or C terminus, or both, of the polypeptide. The functional group may take the form of a binding group, such as a polypeptide, including an antibody domain, an Fc domain or a further structured peptide as described above, capable of binding to a target. It may moreover take the form of a reactive group, capable of chemical bonding with a target. Moreover, it can be an effector group, including large plasma proteins, such as serum albumin, and a cell penetrating peptide.

In a third configuration, a functional group may be attached to the molecular scaffold itself. Examples of functional groups are as for the preceding configuration.

In further embodiments, the polypeptide ligand may comprise a polypeptide linked to a molecular scaffold at n attachment points, wherein said polypeptide is cyclised and forms n separate loops subtended between said n attachment points on the molecular scaffold, wherein n is greater than or equal to 2.

The polypeptide is preferably cyclised by N- to C-terminal fusion, and can be cyclised before or after attachment to the molecular scaffold. Attachment before cyclisation is preferred.

Several methods are known in the art for peptide cyclisation. For example, the polypeptide is cyclised by N—C crosslinking, using a crosslinking agent such as EDC.

In another embodiment, the peptide may be designed to comprise a protected $N^\alpha$ or $C^\alpha$ derivatised amino acid, and cyclised by deprotection of the protected $N^\alpha$ or $C^\alpha$ derivatised amino acid to couple said amino acid to the opposite terminus of the polypeptide.

In a preferred embodiment, the polypeptide is cyclised by enzymatic means.

For example, the enzyme is a transglutaminase, for instance a microbial transglutaminase, such as *Streptomyces mobaraensis* transglutaminase. In order to take advantage of enzymatic cyclisation, it may be necessary to incorporate an N- and/or C-terminal substrate sequence for the enzyme in the polypeptide. Some or all of the substrate sequence(s) can be eliminated during the enzymatic reaction, meaning that the cyclised polypeptide may not comprise the substrate sequences in its final configuration.

In a still further embodiment, the polypeptide ligands according to the invention are specific for human Kallikrein, and may comprise a polypeptide with at least three reactive groups, separated by at least two loop sequences, and a molecular scaffold which forms covalent bonds with the reactive groups of the polypeptide such that at least two polypeptide loops are formed on the molecular scaffold, wherein the loops of the peptide ligand may comprise three, four or five, but less than six, amino acids.

Surprisingly, we have found that peptides which may comprise less than 6 amino acids in each loop can have a much higher binding affinity for Kallikrein.

In one embodiment, the loops of the peptide ligand may comprise three amino acids and the polypeptide has the consensus sequence $G_rFxxG_rRVxG_r$, (SEQ ID NO: 2) wherein $G_r$ is a reactive group.

In another embodiment, the loops of the peptide ligand may comprise five amino acids and a first loop which may comprise the consensus sequence $G_rGGxxNG_r$, (SEQ ID NO: 3) wherein $G_r$ is a reactive group.

For example, two adjacent loops of the polypeptide may comprise the consensus sequence $G_rGGxxNG_rRxxxxG_r$, (SEQ ID NO: 4).

In one embodiment, the loops of the peptide ligand may comprise five amino acids and a first loop may comprise the motif $G_rx^W/_FPx^K/_RG_r$, (SEQ ID NO: 5) wherein $G_r$ is a reactive group. In the present context, the reference to a "first" loop does not necessarily denote a particular position of the loop in a sequence. In some embodiments, however, the first loop may be proximal loop in an amino terminus to carboxy terminus peptide sequence. For example, the polypeptide further may comprise a second, distal loop which may comprise the motif $G_r^T/_LH^Q/_TxLG_r$ (SEQ ID NO: 6). Examples of sequences of the first loop include $G_rxWPAR-G_r$ (SEQ ID NO: 7), $G_rxWPSRG_r$ (SEQ ID NO: 8), $G_rxF-PFRG_r$ (SEQ ID NO: 9) and $G_rxFPYRG_r$ (SEQ ID NO: 10). In these examples, x may be any amino acid, but is for example S or R.

In one embodiment, the loops of the peptide ligand may comprise five amino acids and a first loop may comprise the motif $G_rxHxDLG_r$ (SEQ ID NO: 11), wherein $G_r$ is a reactive group.

In one embodiment, the loops of the peptide ligand may comprise five amino acids and a first loop may comprise the motif $G_rTHxxLG_r$ (SEQ ID NO: 12), wherein $G_r$ is a reactive group.

In one embodiment, the polypeptide may comprise two adjacent loops which may comprise the motif $G_rx^W/_FPx^K/_RG_r^T/_LH^Q/_TDLG_r$ (SEQ ID NO: 13).

In the examples herein, numbering refers to the positions in the loops, and ignores the reactive groups. Thus, in $G_rx^W/_FPx^K/_RG_r^T/_LH^Q/_TDLG_r$ (SEQ ID NO: 13), x is in position 1 and $^T/_L$ in position 6.

In the foregoing embodiments, the reactive group is preferably a reactive amino acid. Preferably, the reactive amino acid is cysteine.

Variants of the polypeptides according to this aspect of the invention can be prepared as described above, by identifying those residues which are available for mutation and preparing libraries which include mutations at those positions.

In a further aspect, there is provided a polypeptide ligand according to the preceding aspect of the invention, which may comprise one or more non-natural amino acid substituents and is resistant to protease degradation.

We have found that certain non-natural amino acids permit binding to plasma Kallikrein with nM Ki, whilst increasing residence time in plasma significantly.

In one embodiment, the non-natural amino acid is selected from N-methyl Arginine, homo-arginine and hydroxyproline. Preferably, N-methyl and homo-derivatives of Arginine are used to replace Arginine, and proline 3 can be preferably replaced by hydroxyproline, azetidine carboxylic acid, or an alpha-substituted amino acid, such as aminoisobutyric acid. In another embodiment, arginine may be replaced with guanidyl-phenylalanine.

In one embodiment, the polypeptide may comprise a first loop which may comprise the motif $G_rxWPARG_r$ (SEQ ID NO: 7), wherein P is replaced with azetidine carboxylic acid; and/or R is replaced with N-methyl arginine; and/or R is replaced with homoarginine; and/or R is replaced with guanidyl-phenylalanine.

In one embodiment, the polypeptide may comprise a first loop which may comprise the motif $G_rxFPYRG_r$ (SEQ ID NO: 10), wherein R is replaced with N-methyl arginine; and/or R is replaced with homoarginine, and wherein proline is replaced by azetidine carboxylic acid; and/or R is replaced with guanidyl-phenylalanine.

In one embodiment, the polypeptide ligand may further comprise a sarcosine polymer, used as a linker to link polypeptide ligands together, or to attach one or more functional groups.

In some embodiments, the polypeptide ligand may be protease resistant. Protease resistant conjugates can be selected by screening a repertoire of polypeptide ligands for protease resistance. Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE FIGURES

The following detailed description, given by way of example, but not intended to limit the invention solely to the specific embodiments described, may best be understood in conjunction with the accompanying drawings.

FIG. 1A-B: Assessment of the reaction conditions for linking phage displayed peptides to tris-(bromomethyl)benzene (TBMB). (A) Molecular mass of the GCGSGCGS-GCG-D1-D2 fusion protein ("GCGSGCGSGCG" disclosed as SEQ ID NO: 14) before and after reaction with 10 μM TBMB in 20 mM NH$_4$HCO$_3$, 5 mM EDTA, pH 8, 20% ACN at 30° C. for 1 hour determined by mass spectrometry. The mass difference of the reacted and non-reacted peptide fusion protein corresponds to the mass of the small molecule core mesitylene. FIG. 1A discloses "ACGSGCGSGCG" as SEQ ID NO: 19. (B) Titres (transducing units) of phage reduced and treated with various concentrations of TBMB in 20 mM NH$_4$HCO$_3$, 5 mM EDTA, pH 8, 20% ACN at 30° C. for 1 hour. Titres of phage from fdg3p0ss21 (black) and from library 1 (white) are shown.

DETAILED DESCRIPTION OF THE INVENTION

Figure 2A:
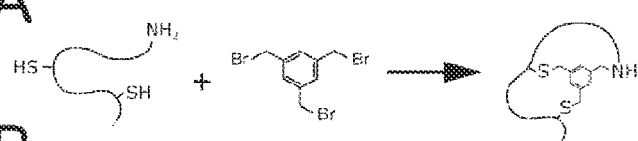
FIG. 2A-D: Chemical reaction of the tri-functional compound TBMB with peptides containing one or two cysteines. (A) Plausible reaction mechanism of TBMB with a peptide fusion protein containing two cysteine residues. (B) Mass spectra of a peptide fusion proteins with two cysteines before and after reaction with TBMB (SEQ ID NOS 16 and 16, respectively, in order of appearance). (C) Plausible reaction mechanism of TBMB with a peptide fusion protein containing one cysteine residue. (D) Mass spectra of a peptide fusion proteins with one cysteine before and after reaction with TBMB (SEQ ID NOS 17 and 17, respectively, in order of appearance).

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4$^{th}$ ed., John Wiley & Sons, Inc.), which are incorporated herein by reference.

A (poly)peptide ligand or (poly)peptide conjugate, as referred to herein, refers to a polypeptide covalently bound to a molecular scaffold. Typically, such polypeptides may comprise two or more reactive groups which are capable of forming covalent bonds to the scaffold, and a sequence subtended between said reactive groups which is referred to as the loop sequence, since it forms a loop when the peptide is bound to the scaffold. In the present case, the polypeptides may comprise at least three reactive groups, and form at least two loops on the scaffold.

The reactive groups are groups capable of forming a covalent bond with the molecular scaffold. Typically, the reactive groups are present on amino acid side chains on the peptide. Examples are amino-containing groups such as cysteine, lysine and selenocysteine.

Specificity, in the context herein, refers to the ability of a ligand to bind or otherwise interact with its cognate target to the exclusion of entities which are similar to the target. For example, specificity can refer to the ability of a ligand to inhibit the interaction of a human enzyme, but not a homologous enzyme from a different species. Using the approach described herein, specificity can be modulated, that is increased or decreased, so as to make the ligands more or less able to interact with homologues or paralogues of the intended target. Specificity is not intended to be synonymous with activity, affinity or avidity, and the potency of the action of a ligand on its target (such as, for example, binding affinity or level of inhibition) are not necessarily related to its specificity.

Binding activity, as used herein, refers to quantitative binding measurements taken from binding assays, for example as described herein. Therefore, binding activity refers to the amount of peptide ligand which is bound at a given target concentration.

Multispecificity is the ability to bind to two or more targets. Typically, binding peptides are capable of binding to a single target, such as an epitope in the case of an antibody, due to their conformational properties. However, peptides can be developed which can bind to two or more targets; dual specific antibodies, for example. In the present invention, the peptide ligands can be capable of binding to two or more targets and can therefore be multispecific. Preferably, they bind to two targets, and are dual specific. The binding may be independent, which would mean that the binding sites for the targets on the peptide are not structurally hindered by the binding of one or other of the targets. In this case both targets can be bound independently. More generally it is expected that the binding of one target will at least partially impede the binding of the other.

A target is a molecule or part thereof to which the peptide ligands bind or otherwise interact with. Although binding is seen as a prerequisite to activity of most kinds, and may be an activity in itself, other activities are envisaged. Thus, the present invention does not require the measurement of binding directly or indirectly.

The molecular scaffold is any molecule which is able to connect the peptide at multiple points to impart one or more structural features to the peptide. It is not a cross-linker, in that it does not merely replace a disulphide bond; instead, it provides two or more attachment points for the peptide. Preferably, the molecular scaffold may comprise at least three attachment points for the peptide, referred to as scaffold reactive groups. These groups are capable of reacting to the reactive groups on the peptide to form a covalent bond. Preferred structures for molecular scaffolds are described below.

Screening for binding activity (or any other desired activity) is conducted according to methods well known in the art, for instance from phage display technology. For example, targets immobilised to a solid phase can be used to identify and isolate binding members of a repertoire. Screening allows selection of members of a repertoire according to desired characteristics.

The term library refers to a mixture of heterogeneous polypeptides or nucleic acids. The library is composed of members, which are not identical. To this extent, library is synonymous with repertoire. Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids. Preferably, each individual organism or cell contains only one or a limited number of library members.

In one embodiment, the nucleic acids are incorporated into expression vectors, in order to allow expression of the polypeptides encoded by the nucleic acids. In a preferred aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants.

In one embodiment, a library of nucleic acids encodes a repertoire of polypeptides. Each nucleic acid member of the library preferably has a sequence related to one or more other members of the library. By related sequence is meant an amino acid sequence having at least 50% identity, for example at least 60% identity, for example at least 70% identity, for example at least 80% identity, for example at least 90% identity, for example at least 95% identity, for example at least 98% identity, for example at least 99% identity to at least one other member of the library. Identity can be judged across a contiguous segment of at least 3 amino acids, for example at least 4, 5, 6, 7, 8, 9 or 10 amino acids, for example at least 12 amino acids, for example at least 14 amino acids, for example at least 16 amino acids, for example at least 17 amino acids or the full length of the reference sequence.

A repertoire is a collection of variants, in this case polypeptide variants, which differ in their sequence. Typically, the location and nature of the reactive groups will not vary, but the sequences forming the loops between them can be randomised. Repertoires differ in size, but may be considered to comprise at least $10^2$ members. Repertoires of $10^{11}$ or more members can be constructed.

A set of polypeptide ligands, as used herein, refers to a plurality of polypeptide ligands which can be subjected to selection in the methods described. Potentially, a set can be a repertoire, but it may also be a small collection of polypeptides, from at least 2 up to 10, 20, 50, 100 or more.

A group of polypeptide ligands, as used herein, refers to two or more ligands. In one embodiment, a group of ligands may comprise only ligands which share at least one target specificity. Typically, a group will consist of from at least 2, 3, 4, 5, 6, 7, 8, 9 or 10, 20, 50, 100 or more ligands. In one embodiment, a group consists of 2 ligands.

(i) Molecular Scaffold

Molecular scaffolds are described in, for example, WO2009098450 and references cited therein, particularly WO2004077062 and WO2006078161.

As noted in the foregoing documents, the molecular scaffold may be a small molecule, such as a small organic molecule.

In one embodiment the molecular scaffold may be, or may be based on, natural monomers such as nucleosides, sugars, or steroids. For example the molecular scaffold may comprise a short polymer of such entities, such as a dimer or a trimer.

In one embodiment the molecular scaffold is a compound of known toxicity, for example of low toxicity. Examples of suitable compounds include cholesterols, nucleotides, steroids, or existing drugs such as tamazepam.

In one embodiment the molecular scaffold may be a macromolecule. In one embodiment the molecular scaffold is a macromolecule composed of amino acids, nucleotides or carbohydrates.

In one embodiment the molecular scaffold may comprise reactive groups that are capable of reacting with functional group(s) of the polypeptide to form covalent bonds.

The molecular scaffold may comprise chemical groups as amines, thiols, alcohols, ketones, aldehydes, nitriles, carboxylic acids, esters, alkenes, alkynes, azides, anhydrides, succinimides, maleimides, alkyl halides and acyl halides.

In one embodiment, the molecular scaffold may comprise or may consist of tris(bromomethyl)benzene, especially 1,3,5-Tris(bromomethyl)benzene ('TBMB'), or a derivative thereof.

In one embodiment, the molecular scaffold is 2,4,6-Tris (bromomethyl)mesitylene. It is similar to 1,3,5-Tris(bromomethyl)benzene but contains additionally three methyl groups attached to the benzene ring. This has the advantage that the additional methyl groups may form further contacts with the polypeptide and hence add additional structural constraint.

Other molecular scaffolds include 1,3,5-triacryloyl-1,3,5-triazinane (TATA), N,N',N"-(benzene-1,3,5-triyl)-tris(2-bromoacetamide) (TBAB) and N,N',N"-benzene-1,3,5-triyltris-prop-2-enamide (TAAB). See Chen et al., ChemBioChem 2012, 13, 1032-1038.

The molecular scaffold of the invention contains chemical groups that allow functional groups of the polypeptide of the encoded library of the invention to form covalent links with the molecular scaffold. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

(ii) Polypeptide

The reactive groups of the polypeptides can be provided by side chains of natural or non-natural amino acids. The reactive groups of the polypeptides can be selected from thiol groups, amino groups, carboxyl groups, guanidinium groups, phenolic groups or hydroxyl groups. The reactive groups of the polypeptides can be selected from azide, keto-carbonyl, alkyne, vinyl, or aryl halide groups. The reactive groups of the polypeptides for linking to a molecular scaffold can be the amino or carboxy termini of the polypeptide.

In some embodiments each of the reactive groups of the polypeptide for linking to a molecular scaffold are of the same type. For example, each reactive group may be a cysteine residue. Further details are provided in WO2009098450.

In some embodiments the reactive groups for linking to a molecular scaffold may comprise two or more different types, or may comprise three or more different types. For example, the reactive groups may comprise two cysteine residues and one lysine residue, or may comprise one cysteine residue, one lysine residue and one N-terminal amine.

Cysteine can be employed because it has the advantage that its reactivity is most different from all other amino acids. Scaffold reactive groups that could be used on the molecular scaffold to react with thiol groups of cysteines are alkyl halides (or also named halogenoalkanes or haloalkanes). Examples are bromomethylbenzene (the scaffold reactive group exemplified by TBMB) or iodoacetamide. Other scaffold reactive groups that are used to couple selectively compounds to cysteines in proteins are maleimides. Examples of maleimides which may be used as molecular scaffolds in the invention include: tris-(2-maleimidoethyl)amine, tris-(2-maleimidoethyl)benzene, tris-(maleimido)benzene. Selenocysteine is also a natural amino acid which has a similar reactivity to cysteine and can be used for the same reactions. Thus, wherever cysteine is mentioned, it is typically acceptable to substitute selenocysteine unless the context suggests otherwise.

Lysines (and primary amines of the N-terminus of peptides) are also well suited as reactive groups to modify peptides on phage by linking to a molecular scaffold. However, they are more abundant in phage proteins than cysteines and there is a higher risk that phage particles might become cross-linked or that they might lose their infectivity. Nevertheless, it has been found that lysines are especially useful in intramolecular reactions (e.g. when a molecular scaffold is already linked to the phage peptide) to form a second or consecutive linkage with the molecular scaffold. In this case the molecular scaffold reacts preferentially with lysines of the displayed peptide (in particular lysines that are in close proximity). Scaffold reactive groups that react selectively with primary amines are succinimides, aldehydes or alkyl halides. In the bromomethyl group that is used in a number of the accompanying examples, the electrons of the benzene ring can stabilize the cationic transition state. This particular aryl halide is therefore 100-1000 times more reactive than alkyl halides. Examples of succinimides for use as molecular scaffold include tris-(succinimidyl aminotriacetate), 1,3, 5-Benzenetriacetic acid. Examples of aldehydes for use as molecular scaffold include Triformylmethane. Examples of alkyl halides for use as molecular scaffold include 1,3,5-Tris(bromomethyl)-2,4,6-trimethylbenzene, 1,3,5-Tris(bromomethyl) benzene, 1,3,5-Tris(bromomethyl)-2,4,6-triethylbenzene.

The amino acids with reactive groups for linking to a molecular scaffold may be located at any suitable positions within the polypeptide. In order to influence the particular structures or loops created, the positions of the amino acids having the reactive groups may be varied by the skilled operator, e.g. by manipulation of the nucleic acid encoding the polypeptide in order to mutate the polypeptide produced. By such means, loop length can be manipulated in accordance with the present teaching.

For example, the polypeptide may comprise the sequence $AC(X)_nC(X)_mCG$ (SEQ ID NO: 15), wherein X stands for a random natural amino acid, A for alanine, C for cysteine and G for glycine and n and m, which may be the same or different, are numbers between 3 and 6.

(iii) Reactive Groups of the Polypeptide

The molecular scaffold of the invention may be bonded to the polypeptide via functional or reactive groups on the polypeptide. These are typically formed from the side chains of particular amino acids found in the polypeptide polymer. Such reactive groups may be a cysteine side chain, a lysine side chain, or an N-terminal amine group or any other suitable reactive group. Again, details may be found in WO2009098450.

Examples of reactive groups of natural amino acids are the thiol group of cysteine, the amino group of lysine, the carboxyl group of aspartate or glutamate, the guanidinium group of arginine, the phenolic group of tyrosine or the hydroxyl group of serine. Non-natural amino acids can provide a wide range of reactive groups including an azide, a keto-carbonyl, an alkyne, a vinyl, or an aryl halide group. The amino and carboxyl group of the termini of the polypeptide can also serve as reactive groups to form covalent bonds to a molecular scaffold/molecular core.

The polypeptides of the invention contain at least three reactive groups. Said polypeptides can also contain four or more reactive groups. The more reactive groups are used, the more loops can be formed in the molecular scaffold.

In a preferred embodiment, polypeptides with three reactive groups are generated. Reaction of said polypeptides with a molecular scaffold/molecular core having a three-fold rotational symmetry generates a single product isomer. The generation of a single product isomer is favourable for several reasons. The nucleic acids of the compound libraries encode only the primary sequences of the polypeptide but not the isomeric state of the molecules that are formed upon reaction of the polypeptide with the molecular core. If only one product isomer can be formed, the assignment of the nucleic acid to the product isomer is clearly defined. If multiple product isomers are formed, the nucleic acid cannot give information about the nature of the product isomer that was isolated in a screening or selection process. The formation of a single product isomer is also advantageous if a specific member of a library of the invention is synthesized. In this case, the chemical reaction of the polypeptide with the molecular scaffold yields a single product isomer rather than a mixture of isomers.

In another embodiment of the invention, polypeptides with four reactive groups are generated. Reaction of said polypeptides with a molecular scaffold/molecular core having a tetrahedral symmetry generates two product isomers. Even though the two different product isomers are encoded by one and the same nucleic acid, the isomeric nature of the isolated isomer can be determined by chemically synthesizing both isomers, separating the two isomers and testing both isomers for binding to a target ligand.

In one embodiment of the invention, at least one of the reactive groups of the polypeptides is orthogonal to the remaining reactive groups. The use of orthogonal reactive groups allows the directing of said orthogonal reactive groups to specific sites of the molecular core. Linking strategies involving orthogonal reactive groups may be used to limit the number of product isomers formed. In other words, by choosing distinct or different reactive groups for one or more of the at least three bonds to those chosen for the remainder of the at least three bonds, a particular order of bonding or directing of specific reactive groups of the polypeptide to specific positions on the molecular scaffold may be usefully achieved.

In another embodiment, the reactive groups of the polypeptide of the invention are reacted with molecular linkers wherein said linkers are capable to react with a molecular scaffold so that the linker will intervene between the molecular scaffold and the polypeptide in the final bonded state.

In some embodiments, amino acids of the members of the libraries or sets of polypeptides can be replaced by any natural or non-natural amino acid. Excluded from these exchangeable amino acids are the ones harbouring functional groups for cross-linking the polypeptides to a molecular core, such that the loop sequences alone are exchangeable. The exchangeable polypeptide sequences have either random sequences, constant sequences or sequences with random and constant amino acids. The amino acids with reactive groups are either located in defined positions within the polypeptide, since the position of these amino acids determines loop size.

In one embodiment, a polypeptide with three reactive groups has the sequence $(X)_l Y(X)_m Y(X)_n Y(X)_o$, wherein Y represents an amino acid with a reactive group, X represents a random amino acid, m and n are numbers between 3 and 6 defining the length of intervening polypeptide segments, which may be the same or different, and l and o are numbers between 0 and 20 defining the length of flanking polypeptide segments.

Alternatives to thiol-mediated conjugations can be used to attach the molecular scaffold to the peptide via covalent interactions. Alternatively these techniques may be used in modification or attachment of further moieties (such as small molecules of interest which are distinct from the molecular scaffold) to the polypeptide after they have been selected or isolated according to the present invention—in this embodiment then clearly the attachment need not be covalent and may embrace non-covalent attachment. These methods may be used instead of (or in combination with) the thiol mediated methods by producing phage that display proteins and peptides bearing unnatural amino acids with the requisite chemical reactive groups, in combination with small molecules that bear the complementary reactive group, or by incorporating the unnatural amino acids into a chemically or recombinantly synthesised polypeptide when the molecule is being made after the selection/isolation phase. Further details can be found in WO2009098450 or Heinis, et al., *Nat Chem Biol* 2009, 5 (7), 502-7.

(iv) Combination of Loops to Form Multispecific Molecules

Loops from peptide ligands, or repertoires of peptide ligands, are advantageously combined by sequencing and de novo synthesis of a polypeptide incorporating the combined loops. Alternatively, nucleic acids encoding such polypeptides can be synthesised.

Where repertoires are to be combined, particularly single loop repertoires, the nucleic acids encoding the repertoires are advantageously digested and re-ligated, to form a novel repertoire having different combinations of loops from the constituent repertoires. Phage vectors can include polylinkers and other sites for restriction enzymes which can provide unique points for cutting and religation of the vectors, to create the desired multispecific peptide ligands. Methods for manipulating phage libraries are well known in respect of antibodies, and can be applied in the present case also.

(v) Attachment of Effector Groups and Functional Groups

Effector and/or functional groups can be attached, for example, to the N or C termini of the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains. An effector group may also comprise a hinge region of an antibody (such a region normally being found between the CH1 and CH2 domains of an IgG molecule).

In a further preferred embodiment of this aspect of the invention, an effector group according to the present invention is an Fc region of an IgG molecule. Advantageously, a peptide ligand-effector group according to the present invention may comprise or consist of a peptide ligand Fc fusion having a tβ half-life of a day or more, two days or more, 3 days or more, 4 days or more, 5 days or more, 6 days or more or 7 days or more. Most advantageously, the peptide ligand according to the present invention may comprise or consist of a peptide ligand Fc fusion having a tβ half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of *Drosophila* (Antennapedia), e.g. as described in Chen and Harrison, Biochemical Society Transactions (2007) Volume 35, part 4, p821 "Cell-penetrating peptides in drug development: enabling intracellular targets" and "Intracellular delivery of large molecules and small peptides by cell penetrating peptides" by Gupta et al. in Advanced Drug Discovery Reviews (2004) Volume 57 9637. Examples of short peptides which have been shown to be efficient at translocation through plasma membranes include the 16 amino acid penetratin peptide from *Drosophila* Antennapedia protein (Derossi et al (1994) J Biol. Chem. Volume 269 p10444 "The third helix of the Antennapedia homeodomain translocates through biological membranes"), the 18 amino acid 'model amphipathic peptide' (Oehlke et al (1998) Biochim Biophys Acts Volume 1414 p127 "Cellular uptake of an alpha-helical amphipathic model peptide with the potential to deliver polar compounds into the cell interior non-endocytically") and arginine rich regions of the HIV TAT protein. Non peptidic approaches include the use of small molecule mimics or SMOCs that can be easily attached to biomolecules (Okuyama et al (2007) Nature Methods Volume 4 p153 'Small-molecule mimics of an a-helix for efficient transport of proteins into cells'. Other chemical strategies to add guanidinium groups to molecules also enhance cell penetration (Elson-Scwab et al (2007) J Biol Chem Volume 282 p13585 "Guanidinylated Neomcyin Delivers Large Bioactive Cargo into cells through a heparin Sulphate Dependent Pathway"). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half life of the peptide ligand in vivo may be used.

RGD peptides, which bind to integrins which are present on many cells, may also be incorporated.

In one embodiment, a peptide ligand-effector group according to the invention has a tβ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a tβ half life in the range 12 to 60 hours. In a further embodiment, it will have a tβ half-life of a day or more. In a further embodiment still, it will be in the range 12 to 26 hours.

Functional groups include drugs, such as cytotoxic agents for cancer therapy. These include Alkylating agents such as Cisplatin and carboplatin, as well as oxaliplatin, mechlorethamine, cyclophosphamide, chlorambucil, ifosfamide; Anti-metabolites including purine analogs azathioprine and mercaptopurine) or pyrimidine analogs; plant alkaloids and terpenoids including vinca alkaloids such as Vincristine, Vinblastine, Vinorelbine and Vindesine; Podophyllotoxin and its derivatives etoposide and teniposide; Taxanes, including paclitaxel, originally known as Taxol; topoisomerase inhibitors including camptothecins, irinotecan and topotecan, and type II inhibitors including amsacrine, etoposide, etoposide phosphate, and teniposide. Further agents can include Antitumour antibiotics which include the immunosuppressant dactinomycin (which is used in kidney transplantations), doxorubicin, epirubicin, bleomycin and others.

Possible effector groups also include enzymes, for instance such as carboxypeptidase G2 for use in enzyme/prodrug therapy, where the peptide ligand replaces antibodies in ADEPT.

(vi) Peptide Modification

To develop the bicyclic peptides (Bicycles; peptides conjugated to molecular scaffolds) into a suitable drug-like molecule, whether that be for injection, inhalation, nasal, ocular, oral or topical administration, a number of properties need to be considered. The following at least need to be designed into a given lead Bicycle:

- protease stability, whether this concerns Bicycle stability to plasma proteases, epithelial ("membrane-anchored") proteases, gastric and intestinal proteases, lung surface proteases, intracellular proteases and the like. Protease stability should be maintained between different species such that a Bicycle lead candidate can be developed in animal models as well as administered with confidence to humans
- replacement of oxidation-sensitive residues, such as tryptophan and methionine with oxidation-resistant analogues in order to improve the pharmaceutical stability profile of the molecule
- a desirable solubility profile, which is a function of the proportion of charged and hydrophilic versus hydrophobic residues, which is important for formulation and absorption purposes
- correct balance of charged versus hydrophobic residues, as hydrophobic residues influence the degree of plasma protein binding and thus the concentration of the free available fraction in plasma, while charged residues (in particular arginines) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic residues may reduce irritation at the injection site (were the peptide drug administered subcutaneously)
- a tailored half-life, depending on the clinical indication and treatment regimen. It may be prudent to develop an unmodified molecule for short exposure in an acute illness management setting, or develop a bicyclic peptide with chemical modifications that enhance the plasma half-life, and hence be optimal for the management of more chronic disease states Approaches to stabilise therapeutic peptide candidates against proteolytic degradation are numerous, and overlap with the peptidomimetics field (for reviews see Gentilucci et al, Curr. Pharmaceutical Design, (2010), 16, 3185-203, and Nestor et al, Curr. Medicinal Chem (2009), 16, 4399-418). These include Cyclisation of peptide N- and C-terminal capping, usually N-terminal acetylation and C-terminal amidation.

Alanine scans, to reveal and potentially remove the proteolytic attack site(s).

D-amino acid replacement, to probe the steric requirements of the amino acid side chain, to increase proteolytic stability by steric hindrance and by a propensity of D-amino acids to stabilise β-turn conformations (Tugyi et al (2005) PNAS, 102(2), 413-418).

N-methyl/N-alkyl amino acid replacement, to impart proteolytic protection by direct modification of the scissile amide bond (Fiacco et al, Chembiochem. (2008), 9(14), 2200-3). N-methylation also has strong effect on the torsional angles of the peptide bond, and is believed to aid in cell penetration & oral availability (Biron et al (2008), Angew. Chem. Int. Ed., 47, 2595-99)

Incorporation of non-natural amino acids, i.e. by employing

Isosteric/isoelectronic side chains that are not recognised by proteases, yet have no effect on target potency Constrained amino acid side chains, such that proteolytic hydrolysis of the nearby peptide bond is conformationally and sterically impeded. In particular, these concern proline analogues, bulky sidechains, Cα-disubstituted derivatives (where the simplest derivative is Aib, $H_2N—C(CH_3)_2—COOH$), and cyclo amino acids, a simple derivative being amino-cyclopropylcarboxylic acid)

Peptide bond surrogates, and examples include

N-alkylation (see above, i.e. CO—NR)

Reduced peptide bonds ($CH_2$—NH—)

Peptoids (N-alkyl amino acids, NR—$CH_2$—CO)

Thio-amides (CS—NH)

Azapeptides (CO—NH—NR)

Trans-alkene (RHC=C—)

Retro-inverso (NH—CO)

Urea surrogates (NH—CO—NHR)

Peptide backbone length modulation i.e. $β^{2/3}$-amino acids, (NH—CR—$CH_2$—CO, NH—$CH_2$—CHR—CO), Substitutions on the alpha-carbon on amino acids, which constrains backbone conformations, the simplest derivative being Aminoisobutyric acid (Aib).

It should be explicitly noted that some of these modifications may also serve to deliberately improve the potency of the peptide against the target, or, for example to identify potent substitutes for the oxidation-sensitive amino acids (Trp and Met).

(B) Repertoires, Sets and Groups of Polypeptide Ligands (i) Construction of Libraries Libraries intended for selection may be constructed using techniques known in the art, for example as set forth in WO2004/077062, or biological systems, including phage vector systems as described herein. Other vector systems are known in the art, and include other phage (for instance, phage lambda), bacterial plasmid expression vectors, eukaryotic cell-based expression vectors, including yeast vectors, and the like. For example, see WO2009098450 or Heinis, et al., *Nat Chem Biol* 2009, 5 (7), 502-7.

Non-biological systems such as those set forth in WO2004/077062 are based on conventional chemical screening approaches. They are simple, but lack the power of biological systems since it is impossible, or at least impracticably onerous, to screen large libraries of peptide ligands. However, they are useful where, for instance, only a small number of peptide ligands needs to be screened. Screening by such individual assays, however, may be time-consuming and the number of unique molecules that can be tested for binding to a specific target generally does not exceed $10^6$ chemical entities.

In contrast, biological screening or selection methods generally allow the sampling of a much larger number of different molecules. Thus biological methods can be used in application of the invention. In biological procedures, molecules are assayed in a single reaction vessel and the ones with favourable properties (i.e. binding) are physically separated from inactive molecules. Selection strategies are available that allow to generate and assay simultaneously more than $10^{13}$ individual compounds. Examples for powerful affinity selection techniques are phage display, ribosome display, mRNA display, yeast display, bacterial display or RNA/DNA aptamer methods. These biological in vitro selection methods have in common that ligand repertoires are encoded by DNA or RNA. They allow the propagation and the identification of selected ligands by sequencing. Phage display technology has for example been used for the isolation of antibodies with very high binding affinities to virtually any target.

When using a biological system, once a vector system is chosen and one or more nucleic acid sequences encoding polypeptides of interest are cloned into the library vector, one may generate diversity within the cloned molecules by undertaking mutagenesis prior to expression; alternatively, the encoded proteins may be expressed and selected before mutagenesis and additional rounds of selection are performed.

Mutagenesis of nucleic acid sequences encoding structurally optimised polypeptides is carried out by standard molecular methods. Of particular use is the polymerase chain reaction, or PCR, (Mullis and Faloona (1987) Methods Enzymol., 155: 335, herein incorporated by reference). PCR, which uses multiple cycles of DNA replication catalysed by a thermostable, DNA-dependent DNA polymerase to amplify the target sequence of interest, is well known in the art. The construction of various antibody libraries has been discussed in Winter et al. (1994) Ann. Rev. Immunology 12, 433-55, and references cited therein.

Alternatively, given the short chain lengths of the polypeptides according to the invention, the variants are preferably synthesised de novo and inserted into suitable expression vectors. Peptide synthesis can be carried out by standard techniques known in the art, as described above. Automated peptide synthesisers are widely available, such as the Applied Biosystems ABI 433 (Applied Biosystems, Foster City, Calif., USA).

(ii) Genetically Encoded Diversity

In one embodiment, the polypeptides of interest are genetically encoded. This offers the advantage of enhanced diversity together with ease of handling. An example of a genetically polypeptide library is a mRNA display library. Another example is a replicable genetic display package (rgdp) library such as a phage display library. In one embodiment, the polypeptides of interest are genetically encoded as a phage display library. Thus, in one embodiment the complex of the invention may comprise a replicable genetic display package (rgdp) such as a phage particle. In these embodiments, the nucleic acid may be comprised by the phage genome. In these embodiments, the polypeptide may be comprised by the phage coat.

In some embodiments, the invention may be used to produce a genetically encoded combinatorial library of polypeptides which are generated by translating a number of nucleic acids into corresponding polypeptides and linking molecules of said molecular scaffold to said polypeptides.

The genetically encoded combinatorial library of polypeptides may be generated by phage display, yeast display, ribosome display, bacterial display or mRNA display.

Techniques and methodology for performing phage display can be found in WO2009098450.

In one embodiment, screening may be performed by contacting a library, set or group of polypeptide ligands with a target and isolating one or more member(s) that bind to said target.

In another embodiment, individual members of said library, set or group are contacted with a target in a screen and members of said library that bind to said target are identified.

In another embodiment, members of said library, set or group are simultaneously contacted with a target and members that bind to said target are selected.

The target(s) may be a peptide, a protein, a polysaccharide, a lipid, a DNA or a RNA.

The target may be a receptor, a receptor ligand, an enzyme, a hormone or a cytokine.

The target may be a prokaryotic protein, a eukaryotic protein, or an archeal protein. More specifically the target ligand may be a mammalian protein or an insect protein or a bacterial protein or a fungal protein or a viral protein.

The target ligand may be an enzyme, such as a protease.

It should be noted that the invention also embraces polypeptide ligands isolated from a screen according to the invention. In one embodiment the screening method(s) of the invention may further comprise the step of: manufacturing a quantity of the polypeptide isolated as capable of binding to said targets.

The invention also relates to peptide ligands having more than two loops. For example, tricyclic polypeptides joined to a molecular scaffold can be created by joining the N- and C-termini of a bicyclic polypeptide joined to a molecular scaffold according to the present invention. In this manner, the joined N and C termini create a third loop, making a tricyclic polypeptide. This embodiment need not be carried out on phage, but can be carried out on a polypeptide-molecular scaffold conjugate as described herein. Joining the N- and C-termini is a matter of routine peptide chemistry. In case any guidance is needed, the C-terminus may be activated and/or the N- and C-termini may be extended for example to add a cysteine to each end and then join them by disulphide bonding. Alternatively the joining may be accomplished by use of a linker region incorporated into the N/C termini. Alternatively the N and C termini may be joined by a conventional peptide bond. Alternatively any other suitable means for joining the N and C termini may be employed, for example N—C-cyclization could be done by standard techniques, for example as disclosed in Linde et al. Peptide Science 90, 671-682 (2008) "Structure-activity relationship and metabolic stability studies of backbone cyclization and N-methylation of melanocortin peptides", or as in Hess et al. J. Med. Chem. 51, 1026-1034 (2008) "backbone cyclic peptidomimetic melanocortin-4 receptor agonist as a novel orally administered drug lead for treating obesity". One advantage of such tricyclic molecules is the avoidance of proteolytic degradation of the free ends, in particular by exoprotease action. Another advantage of a tricyclic polypeptide of this nature is that the third loop may be utilised for generally applicable functions such as BSA binding, cell entry or transportation effects, tagging or any other such use. It will be noted that this third loop will not typically be available for selection (because it is not produced on the phage but only on the polypeptide-molecular scaffold conjugate) and so its use for other such biological functions still advantageously leaves both loops 1 and 2 for selection/creation of specificity.

(iii) Phage Purification

In accordance with the present invention, phage purification before reaction with the molecular scaffold is optional. In the event that purification is desired, any suitable means for purification of the phage may be used. Standard techniques may be applied in the present invention. For example, phage may be purified by filtration or by precipitation such as PEG precipitation; phage particles may be produced and purified by polyethylene-glycol (PEG) precipitation as described previously. Details can be found in WO2009098450.

In case further guidance is needed, reference is made to Jespers et al (Protein Engineering Design and Selection 2004 17(10):709-713. Selection of optical biosensors from chemisynthetic antibody libraries.) In one embodiment phage may be purified as taught therein. The text of this publication is specifically incorporated herein by reference for the method of phage purification; in particular reference is made to the materials and methods section starting part way down the right-column at page 709 of Jespers et al.

Moreover, the phage may be purified as published by Marks et al J. Mol. Biol vol 222 pp 581-597, which is specifically incorporated herein by reference for the particular description of how the phage production/purification is carried out.

If phage purification is not desired, culture medium including phage can be mixed directly with a purification resin and a reducing agent (such as TCEP), as set forth in the examples herein.

(iv) Reaction Chemistry

In comparison to the conditions which are set out in WO2009098450 by Heinis et al., the reaction chemistry used in the present invention provides for a rapid and efficient generation of polypeptide ligands displayed on phage. Reactions conditions used in the present invention preferably may comprise the following steps, all preferably conducted at room temperature:

1. Culture medium from which bacterial cells have been removed, containing phage expressing the desired polypeptide(s), is mixed with buffer, reducing agent and resin equilibrated in buffer.
2. The resin is isolated and resuspended in buffer and dilute reducing agent.
3. The polypeptides are exposed to the molecular scaffold and reacted therewith such that the molecular scaffold forms covalent bonds with the polypeptide.
4. The samples are washed to remove excess unreacted scaffold.
5. Phage are eluted from the resin.

The buffer is preferably pH 8.0; it is not necessary to adjust buffer pH in the final solution. Suitable buffers include $NaHCO_3$, initially at pH 8.0. Alternative buffers may be used, including buffers with a pH in the physiological range, including $NH_4CO_3$, HEPES and Tris-hydroxymethyl aminoethane, Tris, Tris-Acetate or MOPS. The $NaHCO_3$ buffer is preferably used at a concentration of 1M, adding 1 ml to a suspension of resin to equilibrate the resin.

The resin is preferably an ion exchange resin. Ion exchange resins are known in the art, and include any material suitable for anion exchange chromatography known in the art, such as an agarose based chromatography material, e.g. sepharoses like Fast Flow or Capto, polymeric synthetic material, e.g. a polymethacrylate such as Toyopearls, polystyrene/divinylbenzene, such as Poros, Source, or cellulose, e.g. Cellufine. In a preferred embodiment, the anion exchange resin material includes, but is not limited to a resin that carries a primary amine as ligand, e.g. amino-hexyl sepharose, benzamidine sepharose, lysine sepharose, or arginine sepharose. In another preferred embodiment, the anion exchange resin material includes, but is not limited to a resin having a positively charged moiety at neutral pH, such as alkylaminoethane, like diethylaminoethane (DEAE), dimethylaminoethane (DMAE), or trimethylaminoethyl (TMAE), polyethyleneimine (PEI), quaternary aminoalkyl, quaternary aminoethane (QAE), quaternary ammonium (Q), and the like.

In step (1), reducing agent is added to a concentration of 1 mM. The dilute reducing agent used in step (2) is preferably at a concentration of 1 µM. Both concentrations are for TCEP, and other values may apply to other reducing agents. The dilute reducing agent is used to maintain the polypeptide in a reduced state prior to reaction with the molecular scaffold. Preferably, a chelating agent is included in the washing step. For example, EDTA may be included.

Alternative reducing agents may be selected from dithiothreitol, thioglycolic acid, thiolactic acid, 3-mercaptopropionic acid, thiomalic acid, 2,3-dimercaptosuccinic acid, cysteine, N-glycyi-L-cysteine, L-cysteinylglycine and also esters and salts thereof, thioglycerol, cysteamine and C1-C4 acyl derivatives thereof, N-mesylcysteamine, N-acetylcysteine, N-mercaptoalkylamides of sugars such as N-(mercapto-2-ethyl) gluconamide, pantetheine, N-(mercaptoalkyl)-co-hydroxyalkylamides, for example those described in patent application EP-A-354 835, N-mono- or N,N-dialkylmercapto-4-butyramides, for example those described in patent application EP-A-368 763, aminomercaptoalkyl amides, for example those described in patent application EP-A-432 000, N-(mercaptoalkyl)succinamic acids and N-(mercaptoalkyl)succinimides, for example those described in patent application EP-A-465 342, alkylamine mercaptoalkyl amides, for example those described in patent application EP-A-514 282, the azeotropic mixture of 2-hydroxypropyl thioglycolate and of (2-hydroxy-1-methyl)ethyl thioglycolate as described in patent application FR-A-2 679 448, mercaptoalkylamino amides, for example those described in patent application FR-A-2 692 481, and N-mercaptoalkylalkanediamides, for example those described in patent application EP-A-653 202.

The conjugation of the molecular scaffold, in the case of TBMB and other scaffolds whose reactive groups are thiol-reactive, is preferably conducted in the presence of acetonitrile. The acetonitrile is preferably at a final concentration of about 20%.

Alternative scaffolds to TBMB are discussed herein.

Unreacted molecular scaffold is removed from the phage by washing. Subsequently, phage can be eluted from the resin, and selected as set forth previously.

Additional steps can also be included in the procedure. Such steps are not mandatory, and do not significantly increase the yield or efficiency of the process.

For example, the phage-containing culture medium, combined with the resin, can be washed prior to reduction with the reducing agent. The reducing agent itself can be added in two steps; in a concentrated form, to effect reduction, and then in dilute form (step 2 above), to maintain the displayed polypeptide in a reduced state.

The timing of the steps can also be varied, without significantly altering the efficiency of the procedure. For example, we have found that reduction in TCEP for 20 minutes is as effective as reduction for 30 minutes. Likewise, reaction with TBMB for 10 minutes does not give a significantly lower level of binding than reaction for 30 minutes.

(v) Magnetic Separation

In an advantageous embodiment, the resin is magnetic. This allows the polypeptide-bearing phage to be isolated by magnetic separation. Magnetic resin beads, such as magnetic sepharose beads, can be obtained commercially from, for example, Bangs Laboratories, Invitrogen, Origene and GE Healthcare. See also U.S. Pat. No. 2,642,514 and GB 1239978. Application of a magnetic field permits isolation of the beads, which results in purification of the polypeptides bound to the beads from the medium in which they are contained.

In one embodiment, the magnetic beads are separated from the medium by insertion of a magnetic probe into the medium. Beads are retained on the magnetic probe, and can be transferred to a washing station, or a different medium. Alternatively, beads can be isolated by applying a magnetic field to the vessel in which they are contained, and removing the medium once the beads are immobilised.

Magnetic separation provides faster, more efficient processing of resins in the method of the invention.

(C) Use of Polypeptide Ligands According to the Invention

Polypeptide ligands selected according to the method of the present invention may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

The peptide ligands of the present invention will typically find use in preventing, suppressing or treating inflammatory states, allergic hypersensitivity, cancer, bacterial or viral infection, and autoimmune disorders (which include, but are not limited to, Type I diabetes, multiple sclerosis, rheumatoid arthritis, systemic lupus erythematosus, Crohn's disease and myasthenia gravis).

In the instant application, the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

Methods for the testing of systemic lupus erythematosus (SLE) in susceptible mice are known in the art (Knight et al. (1978) J Exp. Med., 147: 1653; Reinersten et al. (1978) New Eng. J: Med., 299: 515). Myasthenia Gravis (MG) is tested in SJL/J female mice by inducing the disease with soluble AchR protein from another species (Lindstrom et al. (1988)

Adv. Immunol., 42: 233). Arthritis is induced in a susceptible strain of mice by injection of Type II collagen (Stuart et al. (1984) Ann. Rev. Immunol., 42: 233). A model by which adjuvant arthritis is induced in susceptible rats by injection of mycobacterial heat shock protein has been described (Van Eden et al. (1988) Nature, 331: 171). Thyroiditis is induced in mice by administration of thyroglobulin as described (Maron et al. (1980) J. Exp. Med., 152: 1115). Insulin dependent diabetes mellitus (IDDM) occurs naturally or can be induced in certain strains of mice such as those described by Kanasawa et al. (1984) Diabetologia, 27: 113. EAE in mouse and rat serves as a model for MS in human. In this model, the demyelinating disease is induced by administration of myelin basic protein (see Paterson (1986) Textbook of Immunopathology, Mischer et al., eds., Grune and Stratton, New York, pp. 179-213; McFarlin et al. (1973) Science, 179: 478: and Satoh et al. (1987) J. Immunol., 138: 179).

Generally, the present peptide ligands will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cylcosporine, methotrexate, adriamycin or cisplatinum, and immunotoxins. Pharmaceutical compositions can include "cocktails" of various cytotoxic or other agents in conjunction with the selected antibodies, receptors or binding proteins thereof of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, including without limitation immunotherapy, the selected antibodies, receptors or binding proteins thereof of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counter-indications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that use levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the selected repertoires of polypeptides described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

(D) Mutation of Polypeptides

The desired diversity is typically generated by varying the selected molecule at one or more positions. The positions to be changed are selected, such that libraries are constructed for each individual position in the loop sequences. Where appropriate, one or more positions may be omitted from the selection procedure, for instance if it becomes apparent that those positions are not available for mutation without loss of activity.

The variation can then be achieved either by randomisation, during which the resident amino acid is replaced by any amino acid or analogue thereof, natural or synthetic, producing a very large number of variants or by replacing the resident amino acid with one or more of a defined subset of amino acids, producing a more limited number of variants.

Various methods have been reported for introducing such diversity. Methods for mutating selected positions are also well known in the art and include the use of mismatched oligonucleotides or degenerate oligonucleotides, with or without the use of PCR. For example, several synthetic antibody libraries have been created by targeting mutations to the antigen binding loops. The same techniques could be used in the context of the present invention. For example, the H3 region of a human tetanus toxoid-binding Fab has been randomised to create a range of new binding specificities (Barbas et al. (1992) Proc. Natl. Acad. Sci. USA, 89: 4457). Random or semi-random H3 and L3 regions have been appended to germline V gene segments to produce large libraries with mutated framework regions (Hoogenboom & Winter (1992) R Mol. Biol., 227: 381; Barbas et al. (1992) Proc. Natl. Acad. Sci. USA, 89: 4457; Nissim et al. (1994) EMBO J, 13: 692; Griffiths et al. (1994) EMBO J, 13: 3245; De Kruif et al. (1995) J. Mol. Biol., 248: 97). Such diversification has been extended to include some or all of the other antigen binding loops (Crameri et al. (1996) Nature Med., 2: 100; Riechmann et al. (1995) BiolTechnology, 13: 475; Morphosys, WO97/08320, supra).

However, since the polypeptides used in the present invention are much smaller than antibodies, the preferred method is to synthesise mutant polypeptides de novo. Mutagenesis of structured polypeptides is described above, in connection with library construction.

The invention is further described below with reference to the following examples.

EXAMPLES

Comparative Example 1

This example is taken from WO2009/098450.

In this example we demonstrate attaching phage displayed peptides to small molecules. The polypeptide in this example is a phage displayed peptide. The nucleic acid is comprised by the phage particle. The molecular scaffold in this example is a small molecule (TBMB).

Typically $10^{11}$-$10^{12}$ t.u. of PEG purified phage were reduced in 20 ml of 20 mM $NH_4HCO_3$, pH 8 with 1 mM TCEP at 42° C. for 1 hr. The phage were spun at 4000 rpm in a vivaspin-20 filter (MWCO of 10,000) to reduce the volume of the reduction buffer to 1 ml and washed twice with 10 ml ice cold reaction buffer (20 mM $NH_4HCO_3$, 5 mM EDTA, pH 8). The volume of the reduced phage was adjusted to 32 ml with reaction buffer and 8 ml of 50 µM TBMB in ACN were added to obtain a final TBMB concentration of 10 µM. The reaction was incubated at 30° C. for 1 hr before non-reacted TBMB was removed by precipitation of the phage with 1/5 volume of 20% PEG, 2.5 M NaCl on ice and centrifugation at 4000 rpm for 30 minutes.

We used the small organic compound tris-(bromomethyl) benzene (TBMB) as a scaffold to anchor peptides containing three cysteine residues (Kemp, D. S. and McNamara, P. E., J. Org. Chem, 1985; FIG. 1B). Halogen alkanes conjugated to an aromatic scaffold react specifically with thiol groups of cysteines in aqueous solvent at room temperature (Stefanova, H. I., Biochemistry, 1993). Meloen and co-workers had previously used bromomethyl-substituted synthetic scaffolds for the immobilization of peptides with multiple cysteines (Timmerman, P. et al., ChemBioChem, 2005). The mild conditions needed for the substitution reaction are convenient to spare the functionality of the phage (Olofsson, L., et al., J. of Molecular Recognition, 1998). We chose cysteines as anchoring points because their side chains have the most distinguished reactivity within the 20 natural amino acids. Also, cysteine residues are rare in proteins of the phage coat (8 cysteines in pIII, one cysteine in pVI, pVII and pIX; Petrenko, V. A. and Smith, G. P., Phage Display in Biotechnology and Drug Discovery, 2005). The three-fold rotational symmetry of the TBMB molecule ensures the formation of a unique structural and spatial isomer upon reaction with three cysteines in a peptide.

Figure 2B:
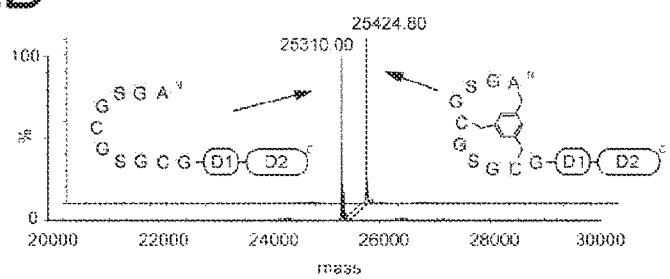
Figure 2C:
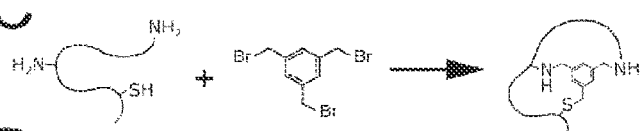
Figure 2D:
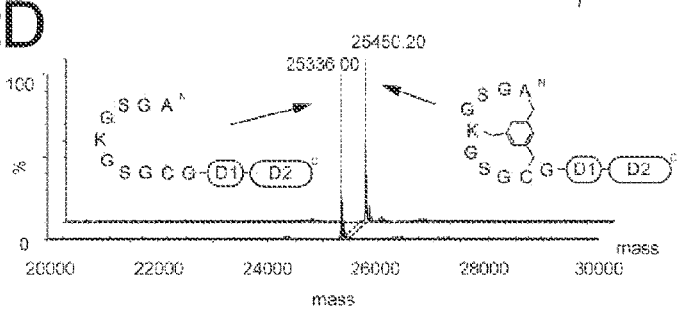

The reaction conditions for the modification of a peptide on phage were elaborated next. As it appeared difficult to detect the chemically modified peptide on phage with available techniques, we expressed the peptide $^N$GCGSGCGSG CG$^C$ (SEQ ID NO: 14) as an N-terminal fusion with the two soluble domains D1 and D2 of the minor phage coat protein pIII and analyzed the molecular weight of the protein before and after reaction with TBMB by mass spectrometry. Attempts to selectively link the three cysteines in the peptide to the scaffold but spare the three disulfide bridges of the D1 and D2 domains of pIII (C7-C36, C46-C53, C188-C201) failed. This prompted us to take advantage of a disulfide-free gene-3-protein recently developed by Schmidt F. X. and co-workers (Kather, I. et al., J. Mol. Biol., 2005). The peptide fused to the N-terminal domain of the cysteine-free gIII protein was reduced with tris(carboxyethyl)phosphine (TCEP). As the reducing agent was found to react with the bromomethyl groups of the TBMB scaffold, it was removed before the addition of TBMB to the protein. Re-oxidation of the thiol groups after removal of TCEP could be prevented by degassing of the reaction buffer and complexation of metal ions with 5 mM EDTA. Reaction of the thiol groups with TBMB at various concentrations and mass spectrometric analysis of the product revealed that a concentration of 10 µM TBMB is sufficient for quantitative modification of the peptide at 30° C. in one hour. Predominantly one product was formed with the expected molecular mass (Δ mass expected=114 Da; FIG. 1A). When the disulfide-free D1-D2 without a fused peptide was incubated with TBMB, its mass was not changed indicating that non-specific reactions with other amino acids do not occur. Addition of phage particles to the reactions ($10^{10}$ t.u. per milliliter) revealed that the high density of phage coat proteins in the vessel does not encumber the reaction of the peptide with TBMB. Unexpectedly, we found that reaction of TBMB with peptides containing only two cysteine residues ($^N$AGSGCGSGCG$^C$-D1-D2) ("AGSGCGSGCG" disclosed as SEQ ID NO: 16) yields a product with a molecular mass that is consistent with the reaction of the remaining bromomethyl group with the primary amine of the N-terminus (FIGS. 2A and 2B). Similarly, the reaction of TBMB with a peptide having one cysteine and a lysine ($^N$AGSGCGSGCG$^C$-D1-D2) ("AGS-GKGSGCG" disclosed as SEQ ID NO: 17) yields a molecular mass that is expected when the primary amines of lysine and the N-terminus react with the remaining two bromomethyl groups (FIGS. 2C and 2D).

Example 2

Comparison of Wild Type Tet and Schmid Phage During Modification

The effect of the TCEP and TBMB modification process on phage infectivity was studied using wild-type (WT) FdTet compared to the mutated Schmid phage, which is disulphide-free. It is believed that Schmid generally has a lower titre, but may be more resistant to chemical modification.

The following phage were tested:
PEP48 peptide in WT FdTet, obtained from S. Luzi (LMB, Cambridge)
PEP48 peptide in Schmid phage obtained from S. Luzi
PK15 in WT FdTet from Edward Walker (Bicycle Therapeutics, Cambridge)

PEP48 and PK15 are two different peptides containing three cysteine residues each. PK15 is specific for kallikrein; PEP48 is specific for mdm2. See European patent Application EP2464727.

Glycerol stocks of these phage were streaked onto tetracycline plates (WT tetracycline (tet) constructs) or chloramphenicol (chlor) plates (Schmid construct).

A single colony of each construct was picked from the plates and used to inoculate 1 ml 2YT/tet or chlor.

Cultures incubated at 37° C. shaking at 250 rpm for ~3 hrs and then made up to 600 ml each in 2 L non-baffled flasks.

Cultures incubated overnight at 37° C., shaking 250 rpm.

The 3×600 ml cultures were then processed as follows to purify the phage:
each 600 ml culture was divided into 2×500 ml centrifuge bottles (6 bottles in total)

bottles were spun at 7500 rpm in JA-10 rotor (=~10000 g) at 4° C. for 20 mins the supernatant was transferred to fresh 500 ml bottles, and samples retained for qPCR 80 ml cold PEG-NaCl was added to each ~300 ml portion the phage were incubated on ice for ~1 hr phage were spun at 7500 rpm in JA-10 rotor (=~10000 g) at 4° C. for 30 mins supernatant was removed phage pellets were resuspended in 5 ml (per construct) TE, and samples retained for qPCR.

The purified phage were assayed by qPCR for particle titre as follows:

serial dilutions of the amplicon were prepared:
   Amplicon supplied as 100 μM=6×10^13 molecules per 1 μl
   10-fold serial dilutions of the amplicon were made in water. A total of 6 dilutions were generated, from lin10^6 to lin10^11. They were stored at −20 C for future use.

primer stock was prepared as follows: 20 μl gene7F2+20 μl gene7R2+60 μl water (∴ 20 μM each primer)

10-fold serial dilutions of the phage samples were prepared, from lin10^3 to lin10^6 in water PCR mastermix was made:
1 μl primer solution
1.75 μl Sigma H$_2$O
0.25 μl 1 μM fluorescein
12 μl SYBRgreen Jumpstart Taq Readymix (Sigma)
Total 15 μl per sample
15 μl mastermix was added to each well of 96 well PCR plate
10 μl of amplicon dilution or phage dilution was added to the wells; the plate was sealed and inserted into BioRad real-time PCR machine
the following programme was run:

```
95° C. 2.5 mins
95° C. 2.5 mins
95° C. 5 min
95° C. 10 sec  ⎫
60° C. 30 sec  ⎬  ×40
+plate read    ⎭
Melt curve
Hold 10° C.
```

The programme was stopped manually when finished
data was extracted from the qPCR machine into Excel and rearranged to form columns of amplicon vs Ct values
sample Ct values were Interpolated from the standard curve.

Figure 8:
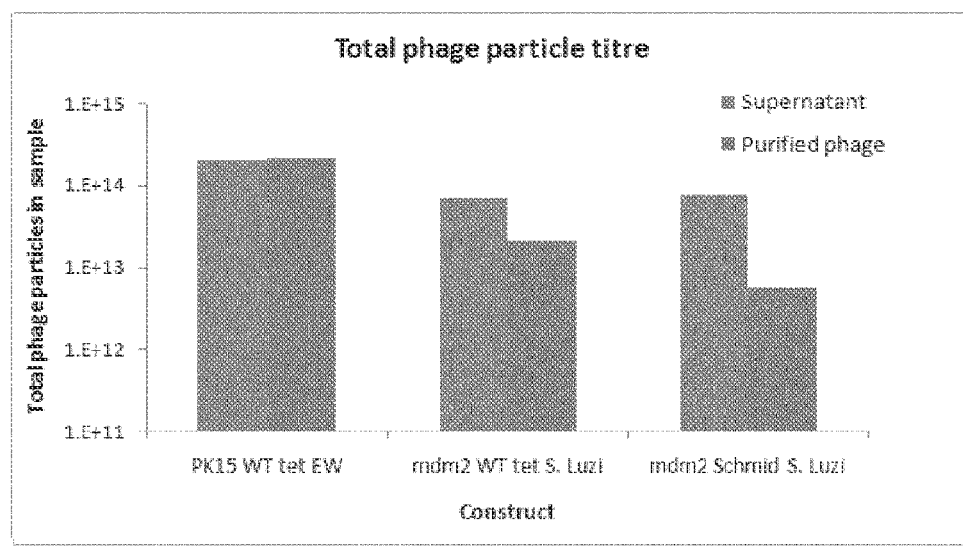
FIG. 8: Bar chart showing total phage titre, comparing wild type and Schmid phage.

The foregoing experiment shows that wild-type and Schmid phage have comparable growth potential when cultured without TBMB (see FIG. 8).

We then tested the comparative efficiency of modification of both wild-type and Schmid phage as a result of exposure to TBMB, such that TBMB is complexed with the displayed polypeptide.

In order to equalise phage concentrations for modification, a portion of each purified phage was diluted in NH$_4$CO$_3$/EDTA buffer {20 mM NH$_4$CO$_3$; 5 mM EDTA; ~pH8.3 (not adjusted); degassed}, so that the final phage concentration was equal to that for PK15 culture supernatant (i.e. 3.4×10^11 per ml). 2.2 ml of diluted phage solution was required:

PK15/WT FdTet: 17.6 μl phage+2128 μl buffer=2.2 ml of 3.4×10^11/ml

PEP48/WT FdTet: 179 μl phage+2021 μl buffer=2.2 ml of 3.4×10^11/ml

PEP48/Schmid: 649 μl phage+1551 μl buffer=2.2 ml of 3.4×10^11/ml

Modification conditions were modified with respect to Heinis et al. Phage modification was carried out in 1 ml NH$_4$CO$_3$/EDTA buffer, including 10 μl 1M Tris pH8. Phage were exposed to 1 mM TCEP for 30 minutes instead of 1 hour, at room temperature rather than 42° C., following which phage were isolated and resuspended in TCEP at 1 μM and immediately re-isolated. Finally, phage were suspended in 800 μl NH4CO3/EDTA buffer+199 μl acetonitrile±60 μM TBMB for 30 minutes, before being isolated and resuspended in 50 μl citrate buffer.

At each stage of phage isolation, phage recovery is not quantitative. "Leftover" phage, not retained in the isolation procedure, are retained for analysis.

The phage eluates (in citrate buffer) were retained. For each construct, a phage sample was modified with TCEP/TBMB, or processed in the absence of TCEP/TBMB.

The leftover input solutions (before treatment) were also retained.

All phage samples, both from purification process and the modification process, were assayed by qPCR (as described above) to determine total number of phage present at each step.

Phage samples from the modification process (inputs, leftover, modified, and not-modified) were assayed for infective titre as follows:

Infective Titre:

An aliquot of HB2151 strain of E. coli was grown in 2YT until OD600=~0.5 This represented ~2.5×10^8 cells/ml phage samples were diluted 1 in 1000 in 2YT 1 μl of diluted samples was added to 1 ml HB2151 (2.5×10^8 cells)

Samples were incubated for 1 hr 37° C. shaking at 250 rpm

7×10-fold serial dilutions were made (neat→10^-7) in 2YT

20 μl of each was spotted onto dried tetracycline agar plates

Plates were incubated overnight at 37° C.

Figure 9A:
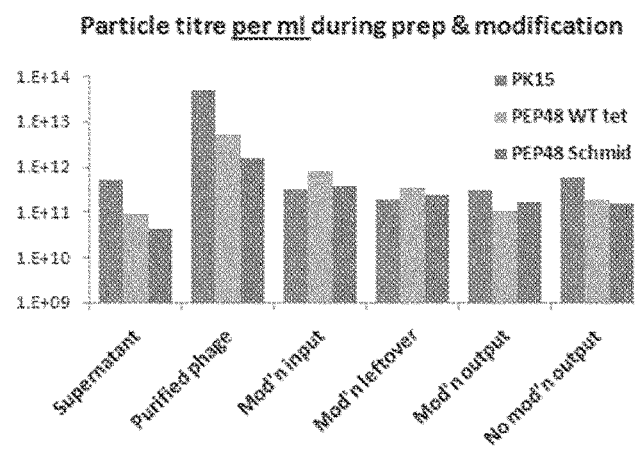
FIG. 9A-B: Phage particle numbers per ml (A) and total (B) during phage preparation and modification, comparing wild type and Schmid phage. In the charts, the left-hand columns are PK15, followed by PEP48 WT, with PEP48 Schmid on the right.
Figure 9B:
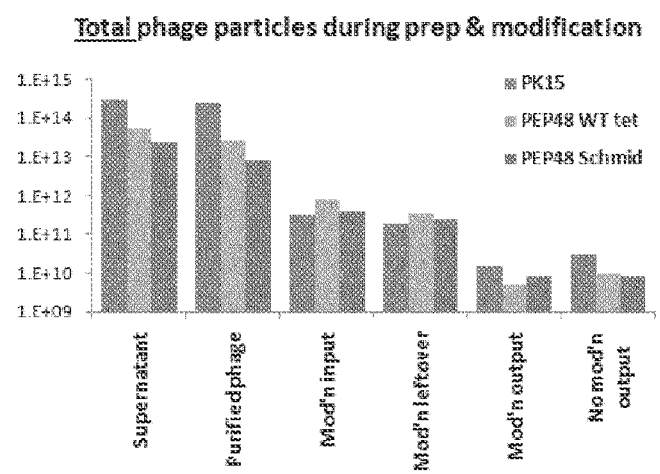

The particle and infective titre data were analysed (see FIGS. 9A and 9B).

| | Total phage particles | | |
|---|---|---|---|
| | PK15 | PEP48 WT tet | PEP48 Schmid |
| Supernatant | 3.01E+14 | 5.63E+13 | 2.52E+13 |
| Purified phage | 2.54E+14 | 2.67E+13 | 7.86E+12 |
| Mod'n input | 3.22E+11 | 8.21E+11 | 3.82E+11 |
| Mod'n leftover | 1.91E+11 | 3.53E+11 | 2.42E+11 |
| Mod'n output | 1.47E+10 | 5.13E+09 | 8.18E+09 |
| No mod'n output | 2.95E+10 | 9.64E+09 | 7.70E+09 |

These results confirm that WT and Schmid phage perform comparably in a modification protocol, with similar numbers of phage being isolatable from each procedural step.

We performed a second experiment, in which comparable phage titres were obtained. We also compared the infective titres of the phage obtained. We found that Schmid phage was considerably less infective than wild-type phage, even in the absence of modification. When modified, the infectivity of the Schmid phage was reduced, compared to wild-type phage.

Particle vs infective titres per ml

|  |  | Titre | | |
| --- | --- | --- | --- | --- |
|  |  | Particle | Infective | Ratio |
| PK15 | Mod'n input | 4.77E+11 | 5.62E+10 | 8.5 |
|  | Mod'n output | 5.41E+11 | 1.00E+10 | 54.1 |
|  | No mod'n output | 6.13E+11 | 1.90E+10 | 32.2 |
| PEP48 WT tet | Mod'n input | 2.71E+11 | 1.08E+10 | 25.2 |
|  | Mod'n output | 1.77E+11 | 1.40E+09 | 126.6 |
|  | No mod'n output | 2.52E+11 | 5.22E+09 | 48.4 |
| PEP48 Schmid | Mod'n input | 5.52E+11 | 1.38E+09 | 401.2 |
|  | Mod'n output | 2.62E+11 | 5.00E+07 | 5.2E+03 |
|  | No mod'n output | 2.61E+11 | 4.75E+08 | 549.5 |

Conclusion

The foregoing experiments demonstrate that wild type and Schmid phage can be used to display peptides in phage libraries. We also showed that the infectivity of Schmid phage is considerably inferior to wild-type phage, in both modified and unmodified conditions.

Example 3

Modification of Phage on Resin

PK15 is a three cysteines containing peptide (H-AC-SDRFRNCPADEALCG-NH$_2$) (SEQ ID NO: 18), which when coupled with TBMB, is a specific and potent inhibitor of human plasma kallikrein. This peptide can be displayed as a fusion to gene 3 protein of phage and if correctly modified by TBMB will result in a phage that can specifically bind to kallikrein. Non-modification of PK15 on the phage or cross-linking of the phage would not result in a specific binding signal for the phage binding to kallikrein.

Anion exchange resin was used to capture the phage, allowing for quick and easy changing of the buffers that the phage were exposed to during the modification process. The phage were also titered for particle number and infectivity to show that the modification process had not made the phage significantly less infectious.

Materials and Methods 1. 1 ml of 1M NaHCO$_3$ was added to either 50 μl, 100 μl or 150 μl of an approximately 50% slurry of a strong anion exchange resin to equilibrate the resin.
2. Each sample was spun at 3000 rpm in a microfuge for one minute before the supernatant was carefully removed.
3. 1 ml of overnight culture, from which the E. coli had been removed by centrifugation, containing PK15 expressing phage was added to each sample, followed by 10 μl of NaHCO$_3$ and 1 μl of 1M TCEP. The NaHCO$_3$ was added to raise the pH of the solution to allow the phage to bind to the resin and the TCEP is a reducing agent. The samples were mixed by rotation for 20 minutes.
4. The samples were centrifuged as before and the supernatant carefully removed.
5. 1 ml of 20 mM NaHCO$_3$, 5 mM EDTA containing 1 μM TCEP was added to re-suspend the resin whilst washing away the majority of the any remaining TCEP prior to the addition of TBMB.
6. The samples were centrifuged and the supernatant carefully removed.
7. 1 ml of 20% acetonitrile in 20 mM NaHCO$_3$, 5 mM EDTA containing 60 μM TBMB was added to each sample. The samples were mixed by rotation for 10 minutes.
8. The samples were centrifuged as before and the supernatant carefully removed.
9. 1 ml of 20 mM NaHCO$_3$, 5 mM EDTA was added to each sample.
10. The samples were centrifuged as before and the supernatant carefully removed.
11. 100 μl of 50 mM citrate pH 5.0, 1.5M NaCl was added to each sample and the samples were mixed for 5 minutes on a shaking platform.
12. Each sample was spun at 13000 rpm in a microfuge for one minute before the supernatant was carefully removed and retained. The supernatant was re-centrifuged, to remove any remaining traces of the resin, and the supernatant was carefully removed and retained.
13. Binding of the phage to kallikrein was performed.

Figure 3:
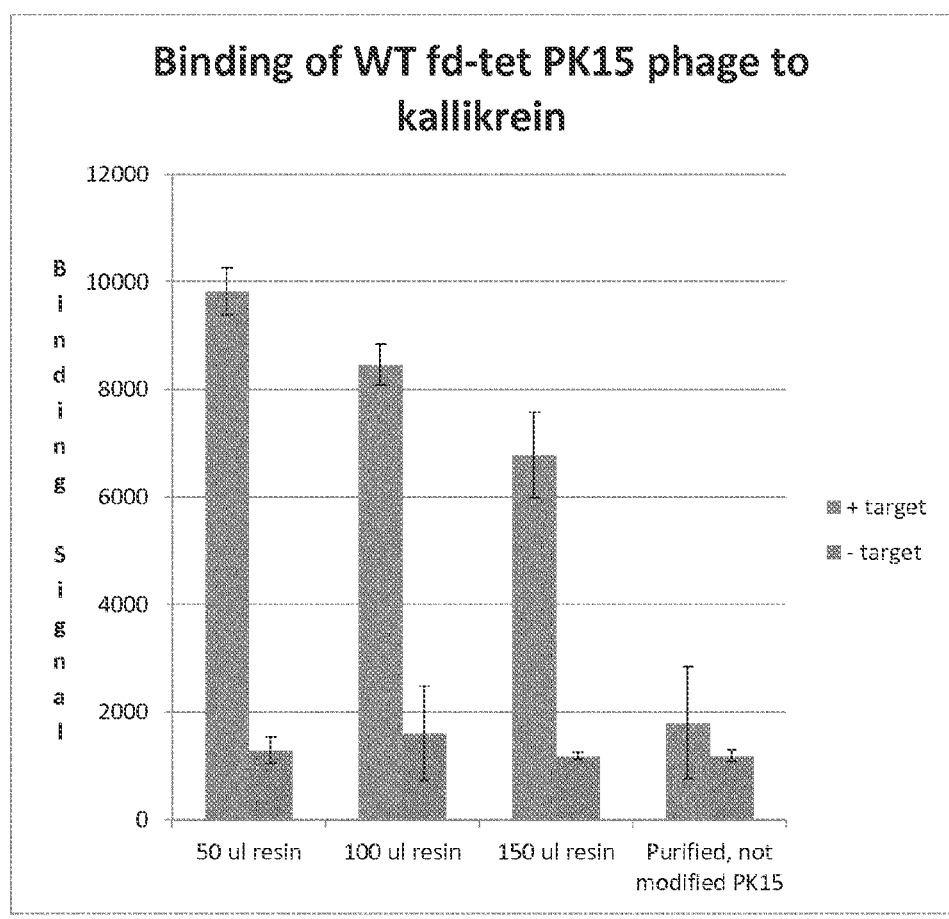
FIG. 3: The binding of resin-processed modified polypeptide ligands to kallikrein is illustrated.

The phage eluted from the resin bound specifically to kallikrein, demonstrating that the modification procedure had successfully created TBMB coupled bicycle peptides on the phage (see FIG. 3).

Phage Titre

The particle and infectious titres for the samples were compared to see if the modification procedure had "damaged" the phage and rendered them less infectious than before the modification.

| | Total phage titre per ml | | |
| --- | --- | --- | --- |
| | Particle | Infective | Ratio |
| 50 μl resin | 3.0E+11 | 2.80E+10 | 10.5 |
| 100 μl resin | 2.9E+11 | 3.40E+10 | 8.6 |
| 150 μl resin | 2.6E+11 | 2.80E+10 | 9.1 |

The roughly 10 fold higher particle titre than infective titre is typical of pre-modification ratio for phage in our laboratories using the standard procedures described above. The modification process has therefore not significantly damaged the phage.

Example 4

Polypeptide Modification on Phage Using Magnetic Separation

The use of a magnetic separation station for the isolation of phage displaying polypeptides is described. In addition, in the present example, the effect of:

Different binding buffers (i.e. phage input solution)

Different binding/wash buffers (i.e. buffer during modification)

Different elution buffers on the efficiency and yield of the magnetic TCEP/TBMB modification process is reviewed. The polypeptide used was PK15, displayed on wild-type FdTet.

Materials and Methods

A colony from E. coli containing PK15/WT FdTet which had been freshly streaked on an agar plate was used to inoculate 25 ml of either 2TY/tet or LB/tet, and cultures were incubated overnight at 37 C shaking 250 rpm.

The following solutions were prepared:
Elution Buffers:
Citrate solution=100 mM (2×)→pH2.0 (without adjustment)
20 ml portions of the 100 mM citrate buffer were diluted 1-in-2 with water, then pH-adjusted (with NaOH) to
pH3.5
pH4
pH5
10 ml portions of each pH solution were supplemented with NaCl to
1M
1.5M
2M
Binding/Wash/Modification Buffers:
The buffers compared were $NH_4CO_3$ and $NaHCO_3$.
1M (50×) $NaHCO_3$ solution reaches pH9.0 (without adjustment)
20 mM $NaHCO_3$ buffer (using the 1M solution) and 5 mM EDTA added reaches pH9.0 (without adjustment). The 20 mM $NaHCO_3$ buffer was degassed for 1 hr.
Samples to be treated in $NaHCO_3$ buffer were prepared using 1M $NaHCO_3$.
The two PK15 cultures were treated as follows:

| Measured OD600: | PK15 in 2TY = 1.95 | PK15 in LB = 2.056 |
|---|---|---|
| Measured pH: | PK15 in 2TY = pH 8.5 | PK15 in LB = pH 7.5 |

Either 1M Tris pH8 (to 10 mM final) for samples in $NH_4CO_3$ buffer or 1M $NaHCO_3$ (to 20 mM final) for samples in $NaHCO_3$ was added to the cultures and pH as measured:
PK15/2TY/Tris=pH 8
PK15/2TY/$NaHCO_3$=pH 9
PK15/LB/$NaHCO_3$=pH 8
The following solutions at the specified pH were prepared.

| | |
|---|---|
| 1 ml $NH_4CO_3$/EDTA buffer | pH 8 |
| 1 ml $NH_4CO_3$/EDTA buffer + 1 mM TCEP | pH 7 |
| 1 ml $NH_4CO_3$/EDTA buffer + 1 µM TCEP | pH 7 |
| 800 µl $NH_4CO_3$/EDTA buffer + 199 µl acetonitrile + 60 µM TBMB | pH 7 |
| 1 ml $NaHCO_3$/EDTA buffer | pH 8 |
| 1 ml $NaHCO_3$/EDTA buffer + 1 mM TCEP | pH 7 |
| 1 ml $NaHCO_3$/EDTA buffer + 1 µM TCEP | pH 7 |
| 800 µl $NaHCO_3$/EDTA buffer + 199 µl acetonitrile + 60 µM TBMB | pH 7 |

Magnetic separation of the chromatography was performed, retaining either the beads or the supernatant where appropriate.
Part A:
For each sample 20 µl magnetic ion exchange beads were rinsed in 1 ml $NH_4CO_3$/EDTA buffer and were resuspended in 10 µl of the same buffer. The samples were then processed as follows
A. 980 µl phage solution+10 µl washed beads+10 µl 1M Tris pH8
B. The samples were mixed for 20 minutes before the beads were magnetically separated from the solution and the beads were retained.
C. The beads were washed with 1 ml of either $NaHCO_3$ or $NH_4CO_3$/EDTA buffer with 1 minute's mixing before capturing the beads magnetically.
D. The beads were washed with 1 ml of either $NaHCO_3$ or $NH_4CO_3$/EDTA+1 mM TCEP buffer with 20 minutes mixing before capturing the beads magnetically. The beads were washed with 1 ml of either $NaHCO_3$ or $NH4CO_3$/EDTA buffer+1 µM TCEP buffer with 1 minutes mixing before capturing the beads magnetically.
E. The beads were then added to 800 µl either $NaHCO_3$ or $NH_4CO_3$/EDTA buffer+200 µl acetonitrile/300 µM TBMB (60 µM TBMB final concentration) and allowed to mix for 30 minutes before capturing the beads magnetically
F. The beads were washed with 1 ml of either $NaHCO_3$ or $NH_4CO_3$/EDTA buffer with 1 minute's mixing before capturing the beads magnetically.
G. The beads were then added to 50 µl 50 mM citrate elution buffer (pH 3.5/4/5; NaCl 1M/1.5M/2M) for 1 minute with mixing.
H. The beads were then captured magnetically and the supernatant retained.
Finally, 10 µl of 1M Tris pH8 was added to the 50 µl eluate to neutralise it.
Samples Performed:

| | Input (binding) | | | | Elution | |
|---|---|---|---|---|---|---|
| | | | | Modification | | |
| # | Media | Phage | Buffer | Buffer | pH | [NaCl] |
| 1 | 2TY | Culture | 10 mM Tris pH 8 | $NH_4CO_3$/EDTA | 4 | 1.5 |
| 2 | 2TY | Supernatant | 10 mM Tris pH 8 | $NH_4CO_3$/EDTA | 4 | 1.5 |
| 3 | 2TY | Culture | 20 mM $NaHCO_3$ pH 9 | $NaHCO_3$/EDTA | 4 | 1.5 |
| 4 | LB | Culture | 20 mM $NaHCO_3$ pH 9 | $NaHCO_3$/EDTA | 4 | 1.5 |
| A | 2TY | Culture | 20 mM $NaHCO_3$ pH 9 | $NaHCO_3$/EDTA | 4 | 1.5 |
| B | 2TY | Culture | 20 mM $NaHCO_3$ pH 9 | $NaHCO_3$/EDTA | 3.5 | 1.5 |
| C | 2TY | Culture | 20 mM $NaHCO_3$ pH 9 | $NaHCO_3$/EDTA | 5 | 1.5 |
| D | 2TY | Culture | 20 mM $NaHCO_3$ pH 9 | $NaHCO_3$/EDTA | 4 | 1 |
| E | 2TY | Culture | 20 mM $NaHCO_3$ pH 9 | $NaHCO_3$/EDTA | 3.5 | 1 |
| F | 2TY | Culture | 20 mM $NaHCO_3$ pH 9 | $NaHCO_3$/EDTA | 5 | 1 |
| G | 2TY | Culture | 20 mM $NaHCO_3$ pH 9 | $NaHCO_3$/EDTA | 4 | 2 |
| H | 2TY | Culture | 20 mM $NaHCO_3$ pH 9 | $NaHCO_3$/EDTA | 3.5 | 2 |
| I | 2TY | Culture | 20 mM $NaHCO_3$ pH 9 | $NaHCO_3$/EDTA | 5 | 2 |

Figure 4A:
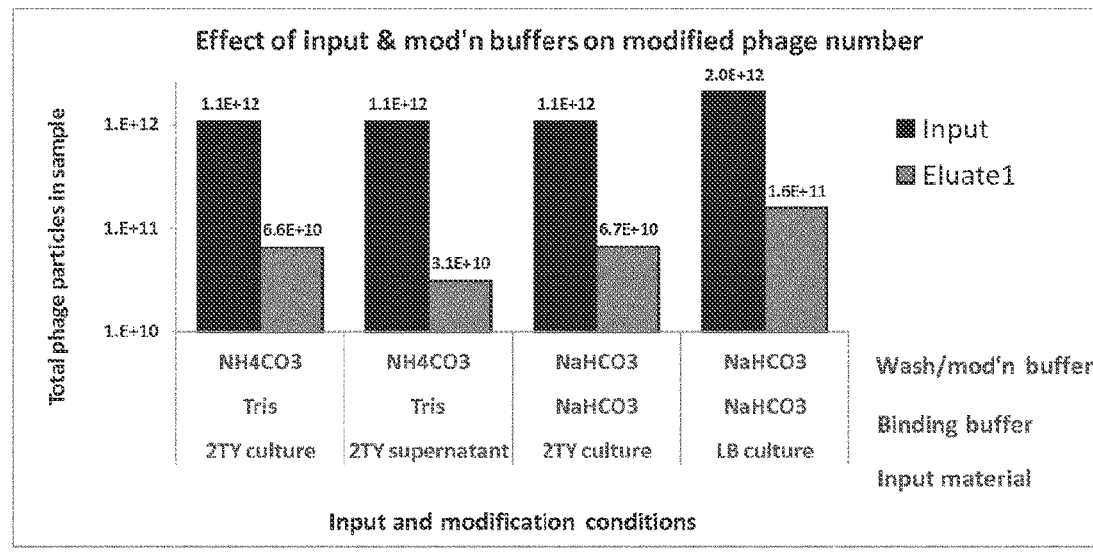
FIG. 4A-C: The effect of different buffers on the performance of the modification procedure. (A) the effect of different modification buffers, NaHCO3 and NH4CO3. (B) The effect of different concentrations of NaCl elution buffer at different pH. (C) The effect of different concentrations of NaCl elution buffer and pH on elution in first and second steps in a two-step elution procedure.
Figure 4B:
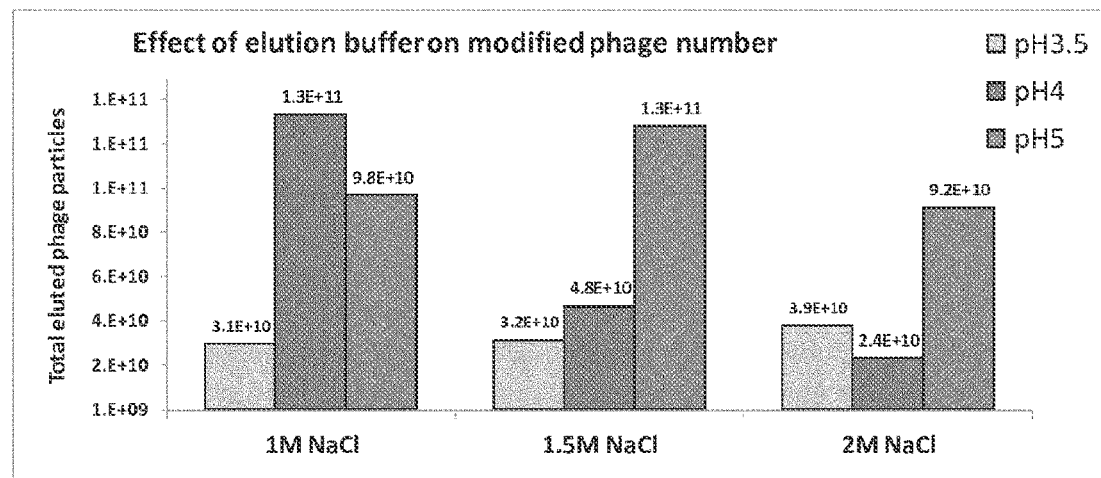
Figure 4:
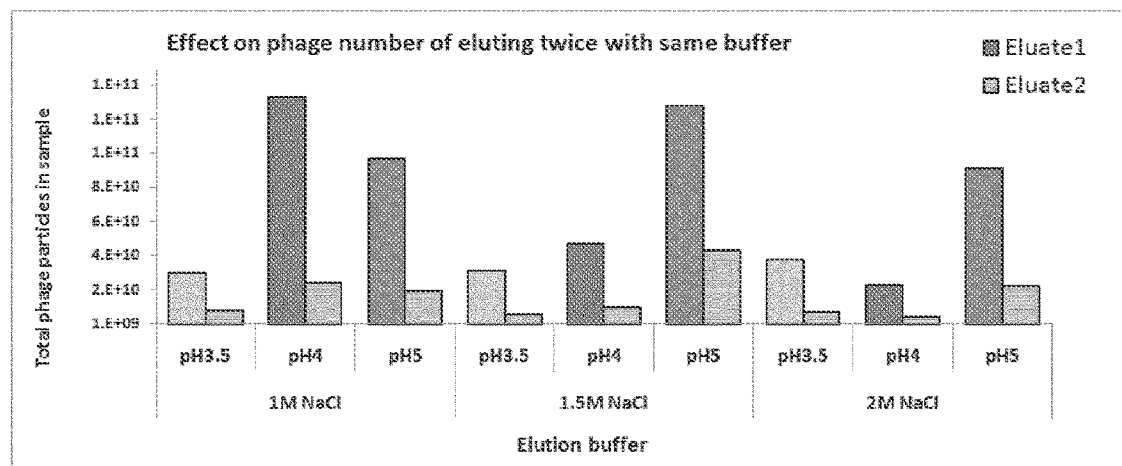

The phage eluates (in citrate buffer) were retained.
In order to see whether each different elution buffer has left any non-eluted phage bound to the beads, a second elution was performed using the same elution buffer.
Samples were assayed by qPCR for particle titre. The results are shown in FIG. 4.
Conclusions:
The nature of the culture media (2TY or LB) does not significantly affect the input phage titre (the 2-fold difference seen is probably within the variability of the qPCR assay).
The nature of the binding buffer (Tris or $NaHCO_3$) does not significantly affect the number of eluted phage
The nature of the wash/modification buffer does not significantly affect the number of eluted phage For all types of input/wash eluted in pH4 1.5M buffer as usual, 30-40% of the input phage are eluted following modification.

There are no clear trends regarding which pH or [NaCl] is best for elution, but:

pH3.5 elution buffer is generally poor

2M NaCl is generally poor

An elution buffer that elutes efficiently in the $1^{st}$ elution, generally elutes well in the $2^{nd}$ elution (even if there may be expected to be less phage retained on the beads after the $1^{st}$ elution).

In order to check the modification of the above samples, the eluted phage were screened for Kallikrein binding.

Figure 5:
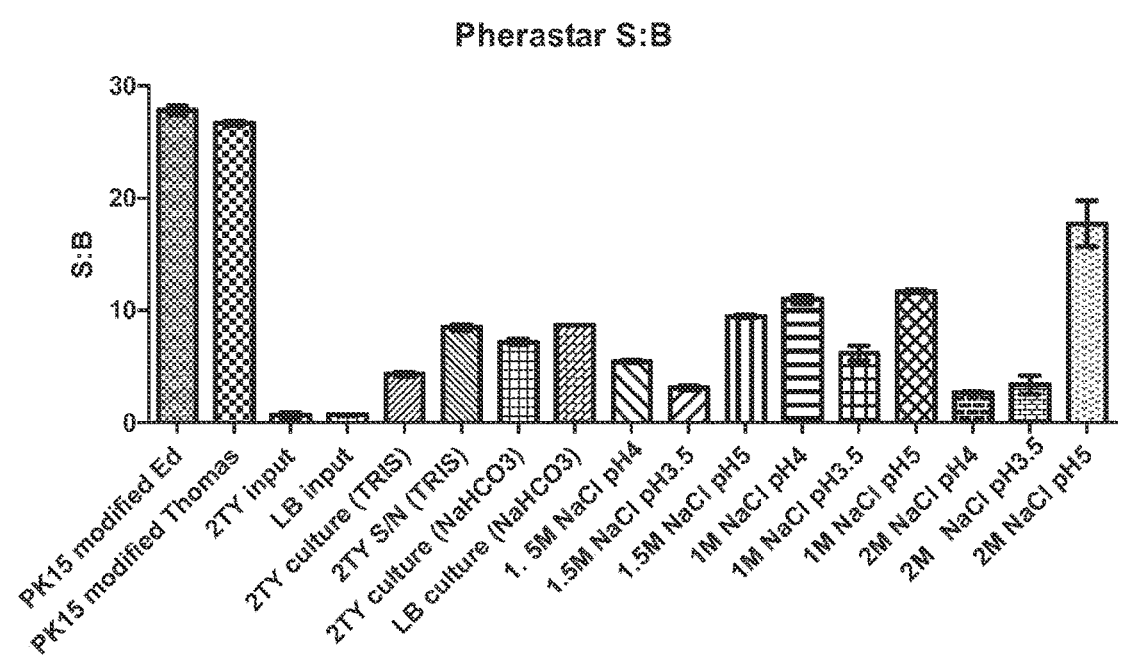
FIG. 5: Target binding assay from the eluates of different samples treated with different buffers and eluted at different pH.

A target binding screen was performed on the eluate samples from above, as shown in FIG. 5. No clear trends were visible, even on repeat assays.

Analysis of Elution Buffers

The binding/elution and modification procedure was repeated with different elution buffers.

Samples performed as set forth below:

| # | Media | Phage | Buffer (Input binding) | Modification Buffer | Elution pH | [NaCl] |
|---|---|---|---|---|---|---|
| 2 | 2TY | Supernatant | 10 mM Tris pH 8 | $NH_4CO_3$/EDTA | 4 | 1.5 |
| 3 | 2TY | Supernatant | 20 mM $NaHCO_3$ pH 9 | $NaHCO_3$/EDTA | 4 | 1.5 |
| 4 | LB | Supernatant | 20 mM $NaHCO_3$ pH 9 | $NaHCO_3$/EDTA | 4 | 1.5 |
| A | 2TY | Supernatant | 20 mM $NaHCO_3$ pH 9 | $NaHCO_3$/EDTA | 4 | 1.5 |
| B | 2TY | Supernatant | 20 mM $NaHCO_3$ pH 9 | $NaHCO_3$/EDTA | 3.5 | 1.5 |
| C | 2TY | Supernatant | 20 mM $NaHCO_3$ pH 9 | $NaHCO_3$/EDTA | 5 | 1.5 |
| D | 2TY | Supernatant | 20 mM $NaHCO_3$ pH 9 | $NaHCO_3$/EDTA | 4 | 1 |
| E | 2TY | Supernatant | 20 mM $NaHCO_3$ pH 9 | $NaHCO_3$/EDTA | 3.5 | 1 |
| F | 2TY | Supernatant | 20 mM $NaHCO_3$ pH 9 | $NaHCO_3$/EDTA | 5 | 1 |
| G | 2TY | Supernatant | 20 mM $NaHCO_3$ pH 9 | $NaHCO_3$/EDTA | 4 | 2 |
| H | 2TY | Supernatant | 20 mM $NaHCO_3$ pH 9 | $NaHCO_3$/EDTA | 3.5 | 2 |
| I | 2TY | Supernatant | 20 mM $NaHCO_3$ pH 9 | $NaHCO_3$/EDTA | 5 | 2 |

Conclusions:

A trend is seen between the eluates from different input samples:

$NH_4CO_3$/Tris/TY<$NaHCO_3$/$NaHCO_3$/TY<$NaHCO_3$/$NaHCO_3$/LB

However the difference between these does not appear to be significant.

Likewise, a trend is seen between the eluates using different elution buffers:

pH 3.5 gives poor elution irrespective of [NaCl]

pH 5 gives best elution when using 1.5M or 2M NaCl pH 4 gives good elution at lower salt pH5 gives the best results, but must be used with high salt.

Example 5

Comparison of 'Quick' and 'Long' Magnetic Phage Modification Protocols

The phage modification process has been optimised from a 'long' protocol. The results of the long protocol are compared herein to a shortened protocol.

A colony from streaked PK15/WT FdTet plate as in Example 3 was used to inoculate 25 ml of 2TY/tet. The culture incubated overnight at 37° C., shaking at 250 rpm.

Figure 6:
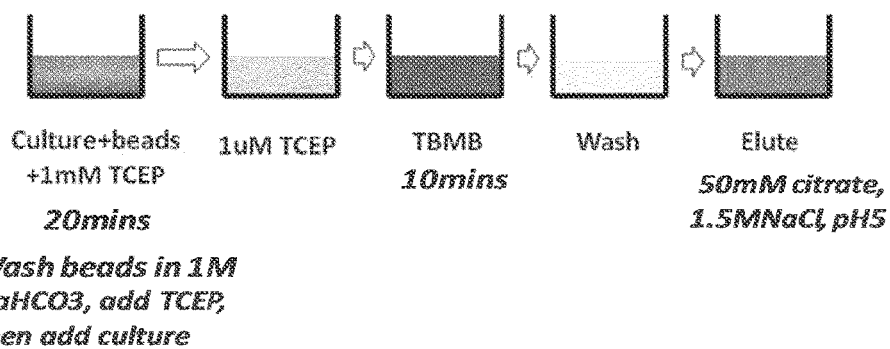
FIG. 6: Illustration of quick and long magnetic modification protocols.
Figure 6:
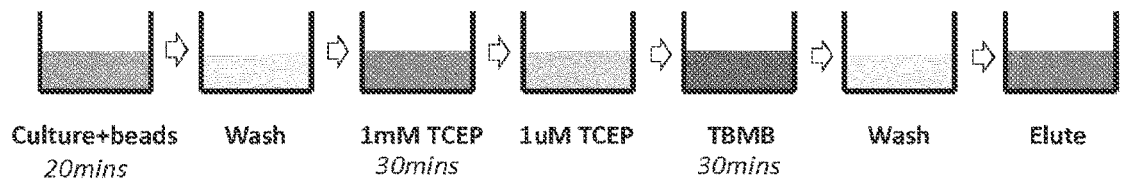

Long and quick protocols were performed. These are illustrated in FIG. 6.

The quick protocol is as follows

Rinse 20 µl magnetic ion exchange beads in 1 ml 1M $NaHCO_3$ buffer and resuspend in 10 µl of the same buffer.

A. 1 ml input solution (Culture/beads/TCEP), mix for 20 minutes and capture the beads magnetically.

B. Wash the beads in 1 ml $NaHCO_3$/EDTA buffer+1 µM TCEP by mixing the beads with the buffer and immediately recapturing the beads magnetically C. Mix the beads in $NaHCO_3$/EDTA buffer+(TBMB in ACN)

where $[ACN]_{final}$=20%; $[TBMB]_{final}$=60 µM for 10 minutes before capturing the beads magnetically D. Wash the beads in 1 ml $NaHCO_3$/EDTA buffer by mixing the beads with the buffer and immediately recapturing the beads magnetically E. Elute the phage from the beads by mixing with 50 µl 50 mM citrate 1.5M NaCl pH5 for 1 minute before magnetically capturing the beads and retaining the supernatant.

Finally, 10 µl of 1M Tris pH8 was added to the 50 µl eluate to neutralise it.

The long protocol is as follows:

Part A:

Rinse 20 µl magnetic ion exchange beads in 1 ml 1M $NaHCO_3$ and resuspend in 10 µl of the same buffer.

A. 980 µl phage solution+10 µl washed beads+10 µl 1M $NaHCO_3$ mix for 20 minutes and capture the beads magnetically.

B. Wash the beads in 1 ml $NaHCO_3$/EDTA buffer by mixing the beads with the buffer and immediately recapturing the beads magnetically C. Mix the beads in 1 ml $NaHCO_3$/EDTA buffer±1 mM TCEP for 30 minutes and capture the beads magnetically.

D. Wash the beads in 1 ml $NaHCO_3$/EDTA buffer±1 µM TCEP by mixing the beads with the buffer and immediately recapturing the beads magnetically E. Mix the beads in $NaHCO_3$/EDTA buffer±(TBMB in ACN) where [ACN]final=20%; [TBMB]final=60 µM for 30 minutes and capture the beads magnetically.

F. Wash the beads in 1 ml $NaHCO_3$/EDTA buffer by mixing the beads with the buffer and immediately recapturing the beads magnetically G. Elute the phage from the beads by mixing with 50 µl 50 mM citrate 1.5M NaCl pH5 for 1 minute before magnetically capturing the beads and retaining the supernatant.

Finally, 10 µl of 1M Tris pH8 was added to the 50 µl eluate to neutralise it.

Samples where TCEP and TBMB had been omitted ('Non-modified') were included.

The infective titre of output samples and input (culture supernatant) was assayed as follows:

E. coli HB2151 were grown and aliquoted in 2YT until OD600=~0.5

This represents ~2.5×10^8 cells/ml

Phage samples were diluted 1in1000 in 2YT

1 µl of diluted samples was added to 1 ml HB2151 (2.5×10^8 cells)

The sample was incubated for 1 hr 37 C shaking 250 rpm

7×10-fold serial dilutions were made (neat→10^-7) in 2YT

Figure 7:
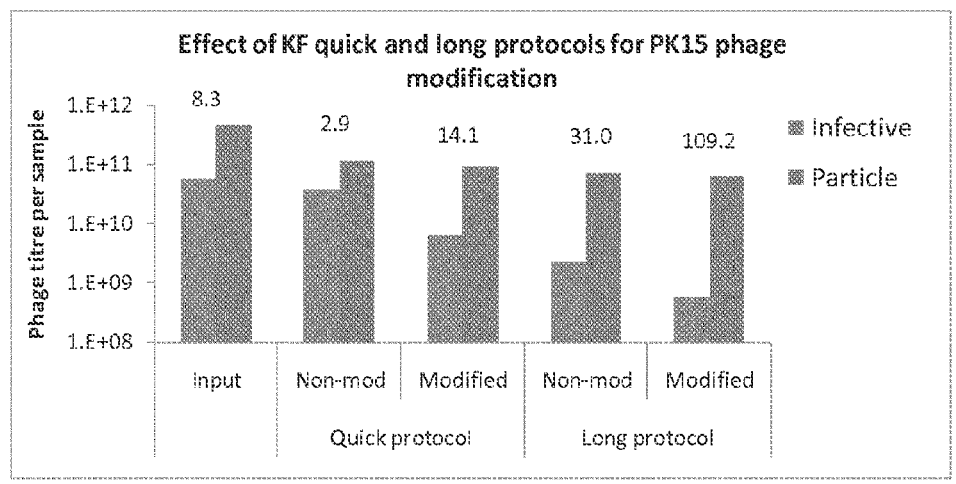
FIG. 7A-B: Comparison of quick and long protocols for modification of PK15-bearing phage: (A) comparison of phage titre by qPCR, and (B) functional comparison for Kallikrein binding.

20 µl of each was spotted onto dried tetracycline agar plates and incubated overnight at 37 C The samples were analysed by qPCR. Results are shown in FIG. 7A.

Figure 7B:
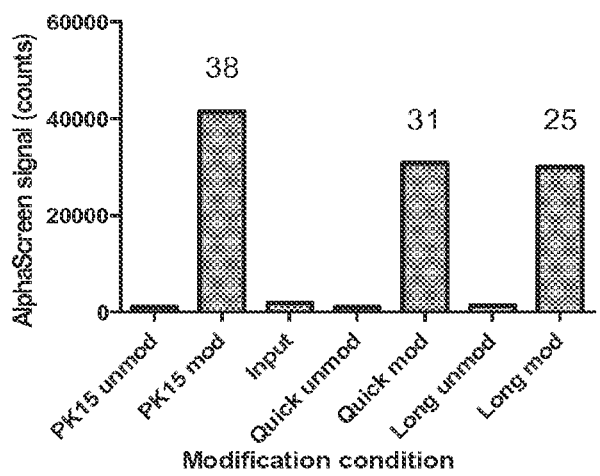

A Kallikrein-binding assay was carried out on the samples in order to check for successful cyclisation. The results are shown in FIG. 7B.

Conclusions:

- The 'Quick' and 'Long' protocols produce modified phage which give similar levels of signal in a kallikrein-binding assay
- Use of the 'Long' protocol is more harmful to the infectivity of the phage than the 'Quick' protocol. The quick protocol retains the ~1-in-10 infective phage as seen in the input; the long protocol reduces the infectivity to 1-in-100.
- Part of the phage damage seen in the long protocol can be attributed to the longer manipulation time (i.e. the 'long' protocol non-modified sample shows some loss of infectivity).
- Overall, use of the new 'Quick' phage modification process leads to good cyclisation without losing infectivity.

Unless otherwise stated, any methods and materials similar or equivalent to those described herein can be used in the practice or testing of the present invention. Methods, devices, and materials suitable for such uses are described above. All publications cited herein are incorporated herein by reference in their entirety for the purpose of describing and disclosing the methodologies, reagents, and tools reported in the publications that might be used in connection with the invention.

The invention is further described by the following numbered paragraphs:

1. A method for conjugating a peptide displayed on a genetic display system to a molecular scaffold, comprising the steps of:

(a) combining polypeptides displayed on a genetic display system with a purification resin such that the display system is bound to the resin and treating the bound display system with a reducing agent;

(b) exposing the bound display system to the molecular scaffold;

(c) removing unreacted molecular scaffold from the bound display system; and (d) eluting the display system from the purification resin.

2. A method according to paragraph 1, wherein the display system is phage display.

3. A method according to paragraph 2, wherein the phage is a wild-type phage.

4. A method according to any preceding paragraph, wherein step (a) is followed by a washing step before addition of the molecular scaffold 5. A method according to paragraph 4, wherein the display system is washed in a dilute solution of reducing agent.

6. A method according to step 5, wherein the wash solution further comprises a chelating agent.

7. A method according to any preceding paragraph, wherein the reducing agent is TCEP.

8. A method according to any preceding paragraph, wherein the scaffold is TBMB.

9. A method according to any preceding paragraph, wherein the molecular scaffold is added in the presence of aqueous acetonitrile.

10. A method according to any preceding paragraph, wherein the resin is an anion exchange resin.

11. A method according to any preceding paragraph, wherein the resin is magnetic.

12. A method according to any preceding paragraph, wherein one or both of steps (a) and (b) is performed at room temperature (25° C.).

13. A method according to any preceding paragraph, wherein step (a) is performed for 20 minutes.

14. A method according to any preceding paragraph, wherein step (b) is performed for 10 minutes.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for conjugating a peptide displayed on a phage display system to a molecular scaffold, comprising the steps of:
    (a) combining polypeptides displayed on a phage display system with a purification resin such that the phage display system is bound to the resin and treating the bound phage display system with a reducing agent;
    (b) exposing the bound phage display system to the molecular scaffold;
    (c) removing unreacted molecular scaffold from the bound phage display system; and
    (d) eluting the phage display system from the purification resin.

2. A method according to claim 1, wherein the phage is a wild-type phage.

3. A method according to claim 1, wherein step (a) is followed by a washing step before addition of the molecular scaffold.

4. A method according to claim 3, wherein the phage display system is washed in a dilute solution of reducing agent.

5. A method according to claim 3, wherein the wash solution further comprises a chelating agent.

6. A method according to claim 1, wherein the reducing agent is TCEP.

7. A method according to claim 1, wherein the scaffold is TBMB.

8. A method according to claim 1, wherein the molecular scaffold is added in the presence of aqueous acetonitrile.

9. A method according to claim 1, wherein the resin is an anion exchange resin.

10. A method according to claim 1, wherein the resin is magnetic.

11. A method according claim 1, wherein one or both of steps (a) and (b) is performed at room temperature (25° C.).

12. A method according to claim 1, wherein step (a) is performed for 20 minutes.

13. A method according to claim 1, wherein step (b) is performed for 10 minutes.

* * * * *